(12) United States Patent
Shimizukawa et al.

(10) Patent No.: US 12,350,079 B2
(45) Date of Patent: Jul. 8, 2025

(54) COMPUTED TOMOGRAPHY APPARATUS

(71) Applicant: FUJIFILM CORPORATION, Tokyo (JP)

(72) Inventors: Sho Shimizukawa, Kanagawa (JP); Takashi Tajima, Kanagawa (JP); Tatsuya Taneichi, Kanagawa (JP); Naoyuki Nishino, Kanagawa (JP); Hisatsugu Horiuchi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 229 days.

(21) Appl. No.: 18/356,161

(22) Filed: Jul. 20, 2023

(65) Prior Publication Data
US 2024/0065652 A1 Feb. 29, 2024

(30) Foreign Application Priority Data
Aug. 23, 2022 (JP) ................................. 2022-132601

(51) Int. Cl.
*A61B 6/00* (2024.01)
*A61B 6/03* (2006.01)
*A61B 6/40* (2024.01)
*A61B 6/04* (2006.01)

(52) U.S. Cl.
CPC ............ *A61B 6/4014* (2013.01); *A61B 6/032* (2013.01); *A61B 6/5247* (2013.01); *A61B 6/54* (2013.01); *A61B 6/0478* (2013.01)

(58) Field of Classification Search
CPC .. A61B 6/032; A61B 6/00; A61B 6/02; A61B 6/025; A61B 6/027; A61B 6/03; A61B 6/037; A61B 6/4429; A61B 6/4417; A61B 6/4452; A61B 8/5261; A61B 8/5238
See application file for complete search history.

(56) References Cited

U.S. PATENT DOCUMENTS

2016/0166223 A1* 6/2016 Besson ................ A61B 6/4007
378/9

FOREIGN PATENT DOCUMENTS

JP 2006-187453 A 7/2006

* cited by examiner

*Primary Examiner* — Don K Wong
(74) *Attorney, Agent, or Firm* — SOLARIS Intellectual Property Group, PLLC

(57) ABSTRACT

A CT apparatus includes a plurality of imaging units, a rotation mechanism, a radiation source elevating mechanism, a detector elevating mechanism, and a CPU. The imaging unit includes a radiation source that emits radiation having a quadrangular pyramid shape to a subject and a radiation detector in which a plurality of pixels detecting the radiation transmitted through the subject are two-dimensionally arranged. The rotation mechanism rotates the plurality of imaging units around a body axis of the subject. The radiation source elevating mechanism and the detector elevating mechanism change an interval between the plurality of imaging units in a rotation axis direction. An imaging control unit of the CPU controls operations of the plurality of imaging units, the rotation mechanism, the radiation source elevating mechanism, and the detector elevating mechanism.

16 Claims, 37 Drawing Sheets

FIG. 15

| | FIRST IMAGING MODE | SECOND IMAGING MODE |
|---|---|---|
| HEIGHT POSITION OF FIRST IMAGING UNIT | UPPER END POSITION | |
| HEIGHT POSITION OF SECOND IMAGING UNIT | LOWER END POSITION | UPPER END POSITION |
| IMAGING RANGE | FIRST IMAGING RANGE EXCEEDING WIDTH OF DETECTION SURFACE OF ONE RADIATION DETECTOR | SECOND IMAGING RANGE WITHIN WIDTH OF DETECTION SURFACE OF ONE RADIATION DETECTOR |
| ROTATION ANGLE | 360° (FIRST SET ANGLE) | 240° (SECOND SET ANGLE) |
| ROTATION DIRECTION | CLOCKWISE (FIRST DIRECTION) | COUNTERCLOCKWISE (SECOND DIRECTION) |
| IMAGING TIME | 10 SECONDS | ABOUT 6.7 SECONDS |
| FRAME RATE | 30 fps (300 view 1.2°/view) | 30 fps (200 view 1.2°/view) |
| ANGLE COVERED BY FIRST IMAGING UNIT | | 0° TO 240° |
| ANGLE COVERED BY SECOND IMAGING UNIT | | 120° TO 360° |

FIG. 23

| | INTERVAL | APPLICATION |
|---|---|---|
| SUB-IMAGING MODE A | INTERVAL AT WHICH LOWER END OF FLUX OF FIRST RADIATION IS MATCHED WITH UPPER END OF FLUX OF SECOND RADIATION | STANDARD IMAGING SUCH AS WHOLE SPINE IMAGING |
| SUB-IMAGING MODE B | INTERVAL AT WHICH MINIMUM OVERLAPPING IMAGING RANGE FOR COMBINING IMAGES CAN BE SECURED | IMAGING OF WIDE RANGE SUCH AS PATIENT WITH SCOLIOSIS |
| SUB-IMAGING MODE C | INTERVAL AT WHICH FLUX OF FIRST RADIATION AND FLUX OF SECOND RADIATION OVERLAP PARTIALLY | IMAGING OF NARROW RANGE SUCH AS CHILD |

| | FIRST IMAGING MODE | SECOND IMAGING MODE |
|---|---|---|
| HEIGHT POSITION OF FIRST IMAGING UNIT | UPPER END POSITION | UPPER END POSITION |
| HEIGHT POSITION OF SECOND IMAGING UNIT | INTERMEDIATE POSITION | |
| HEIGHT POSITION OF THIRD IMAGING UNIT | LOWER END POSITION | |
| IMAGING RANGE | FIRST IMAGING RANGE EXCEEDING WIDTH OF DETECTION SURFACE OF ONE RADIATION DETECTOR | SECOND IMAGING RANGE WITHIN WIDTH OF DETECTION SURFACE OF ONE RADIATION DETECTOR |
| ROTATION ANGLE | 360° (FIRST SET ANGLE) | 120° (SECOND SET ANGLE) |
| ROTATION DIRECTION | CLOCKWISE (FIRST DIRECTION) | COUNTERCLOCKWISE (SECOND DIRECTION) |
| IMAGING TIME | 10 SECONDS | ABOUT 3.3 SECONDS |
| FRAME RATE | 30 fps (300 view 1.2°/view) | 30 fps (100 view 1.2°/view) |
| ANGLE COVERED BY FIRST IMAGING UNIT | | 0° TO 120° |
| ANGLE COVERED BY SECOND IMAGING UNIT | | 120° TO 240° |
| ANGLE COVERED BY THIRD IMAGING UNIT | | 240° TO 360° |

155

COMPUTED TOMOGRAPHY APPARATUS

CROSS-REFERENCE TO RELATED APPLICATIONS

The present application claims priority under 35 U.S.C. § 119 to Japanese Patent Application No. 2022-132601, filed on Aug. 23, 2022. The above application is hereby expressly incorporated by reference, in its entirety, into the present application.

BACKGROUND

1. Technical Field

The technology of the present disclosure relates to a computed tomography apparatus.

2. Description of the Related Art

JP2006-187453A discloses a computed tomography apparatus (hereinafter, referred to as a CT apparatus) that images a subject in a decubitus posture and comprises a plurality of imaging units, each of which includes a radiation source that emits radiation to the subject and a radiation detector that detects the radiation transmitted through the subject, in order to improve the efficiency of image acquisition. The plurality of imaging units are disposed at equal intervals in a gantry that is rotated around a body axis of the subject. The radiation source emits a cone beam, and the radiation detector has a configuration in which a plurality of pixels are two-dimensionally arranged.

SUMMARY

In the related art, the CT apparatus images a relatively wide range of the subject in the body axis direction, such as the whole body or upper body of the subject, or a relatively narrow range of the subject in the body axis direction, such as a suspected part considered to be the cause of a disease. The CT apparatus described in JP2006-187453A can complete the imaging of the relatively narrow range which is the latter case in a short time, but has a problem that it takes a long time to image the relatively wide range which is the former case. In a case in which it takes a long time to perform the imaging, the burden on the subject is increased, and the concern that the quality of the image will deteriorate due to the body movement of the subject is also increased.

An embodiment according to the technology of the present disclosure provides a computed tomography apparatus that can complete both imaging of a relatively wide range and imaging of a relatively narrow range in a short time.

According to the present disclosure, there is provided a computed tomography apparatus comprising: a plurality of imaging units each of which includes a radiation source that emits radiation having a quadrangular pyramid shape to a subject and a radiation detector in which a plurality of pixels detecting the radiation transmitted through the subject are two-dimensionally arranged; a rotation mechanism that rotates the plurality of imaging units around a body axis of the subject; a displacement mechanism that changes an interval between the plurality of imaging units in a rotation axis direction; and a processor that controls operations of the plurality of imaging units, the rotation mechanism, and the displacement mechanism.

Preferably, the processor controls switching between a first imaging mode in which the interval is relatively large for imaging and a second imaging mode in which the interval is relatively small for imaging.

Preferably, the first imaging mode is a mode in which a first imaging range that exceeds a width of a detection surface for the radiation in the radiation detector is imaged, and a rotation angle of the plurality of imaging units around the body axis in the first imaging mode is a first set angle that is equal to or greater than 180°.

Preferably, the processor sets the interval such that an overlapping imaging range occurs between projection images obtained by the imaging units adjacent to each other, performs a reconstruction process on the projection images obtained from each of the plurality of imaging units to generate a plurality of tomographic images for each of the plurality of imaging units, and registers the plurality of tomographic images on the basis of the overlapping imaging range to combine the plurality of tomographic images.

Preferably, the plurality of imaging units have different phases in a rotation direction, the second imaging mode is a mode in which a second imaging range within a width of a detection surface for the radiation in the radiation detector is imaged, a rotation angle of the plurality of imaging units around the body axis in the second imaging mode is a second set angle corresponding to the phases of the plurality of imaging units in the rotation direction, and the plurality of imaging units are rotated at the second set angle such that imaging of an entire circumference around the body axis is shared by the plurality of imaging units.

Preferably, in a case in which the first imaging mode and the second imaging mode are continuously performed, the processor rotates the plurality of imaging units in a first direction in the first imaging mode and rotates the plurality of imaging units in a second direction opposite to the first direction in the second imaging mode.

Preferably, the first imaging mode includes a plurality of sub-imaging modes in which the intervals are different.

Preferably, the radiation detector is disposed at an offset position that is separated from a reference position facing the radiation source by a preset angle as viewed from the rotation axis direction.

Preferably, the plurality of imaging units are held in a frame, and the subject is positioned in the frame. Preferably, the radiation source is disposed outside the frame, and the radiation detector is disposed inside the frame as viewed from the rotation axis direction.

Preferably, the plurality of imaging units are two imaging units of a first imaging unit and a second imaging unit. Preferably, in a case in which a position where a first radiation source of the first imaging unit is disposed is 0° as viewed from the rotation axis direction, a second radiation source of the second imaging unit is disposed at a position separated from the first radiation source by an angle that is equal to or greater than 90° and equal to or less than 120°.

Preferably, the plurality of imaging units are three imaging units.

Preferably, the displacement mechanism has an electric mode in which the imaging unit is moved by an electric actuator and a manual mode in which the imaging unit is manually moved.

Preferably, in the manual mode, the processor performs control to issue a warning in a case in which the interval is equal to or greater than a threshold value.

Preferably, the computed tomography apparatus further comprises a camera that is moved in operative association with the imaging unit. Preferably, the processor performs control to display a camera image obtained from the camera on a display.

Preferably, the processor displays an imaging range that is reconstructible as a tomographic image to be superimposed on the camera image.

Preferably, the subject is positioned in either a standing posture or a sitting posture.

According to the technology of the present disclosure, it is possible to provide a computed tomography apparatus that can complete both the imaging of a relatively wide range and the imaging of a relatively narrow range in a short time.

BRIEF DESCRIPTION OF THE DRAWINGS

Exemplary embodiments according to the technique of the present disclosure will be described in detail based on the following figures, wherein:

FIG. 15 is a table summarizing content of each of a first imaging mode and a second imaging mode;

FIG. 23 is a table illustrating a plurality of sub-imaging modes in which intervals are different;

FIG. 34 is a table summarizing content of each of the first imaging mode and the second imaging mode in a case in which three imaging units are provided;

DETAILED DESCRIPTION

Figure 1:
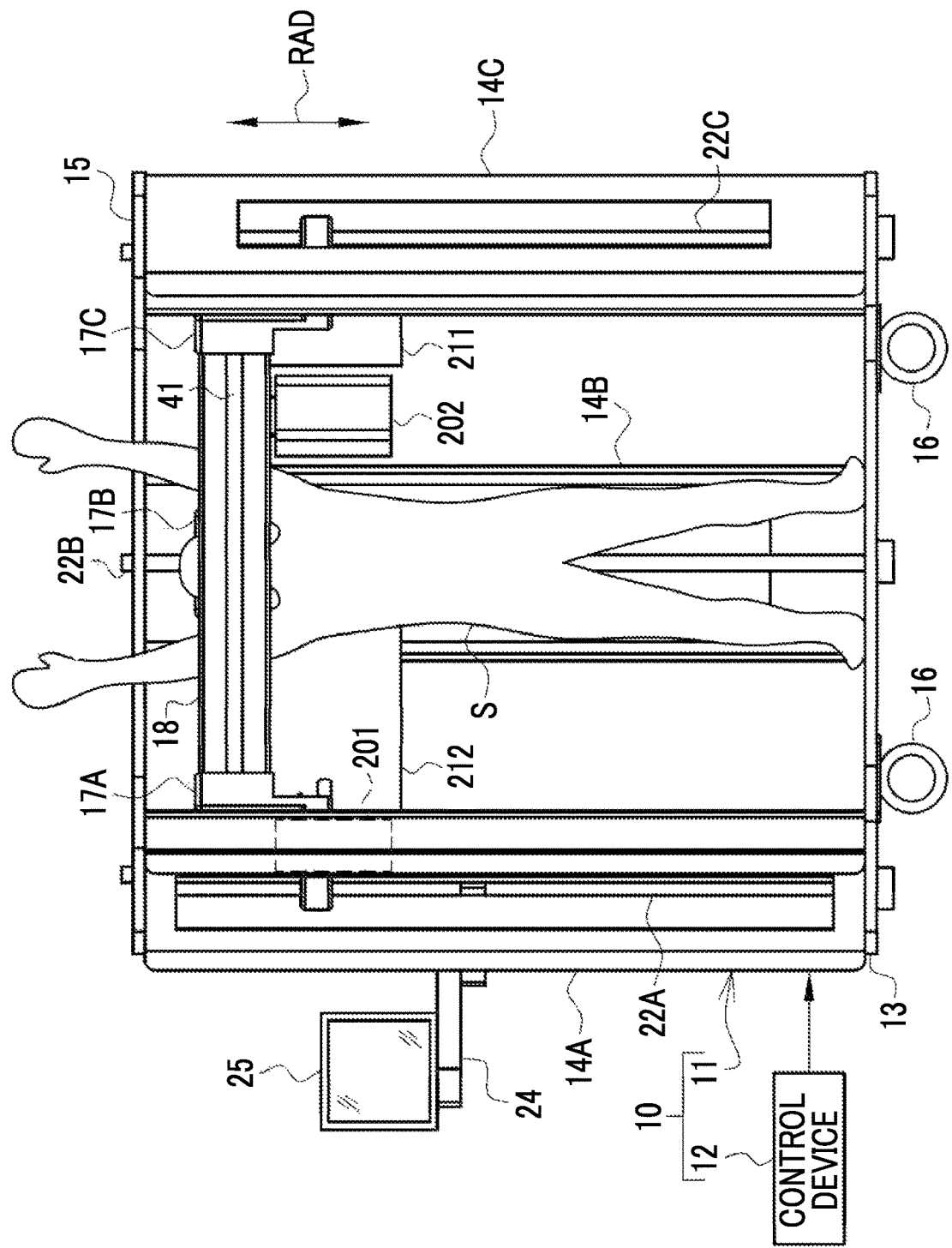
FIG. 1 is a front view illustrating a CT apparatus.

For example, as illustrated in FIG. 1, a CT apparatus 10 is an apparatus for obtaining a tomographic image of a subject S and is composed of an apparatus main body 11 and a control device 12. The apparatus main body 11 is installed, for example, in an imaging room of a medical facility. The control device 12 is installed, for example, in a control room next to the imaging room. The control device 12 is a desktop personal computer, a notebook personal computer, or a tablet terminal. The control device 12 is operated by an operator of the CT apparatus 10 such as a medical radiologist.

Figure 2:
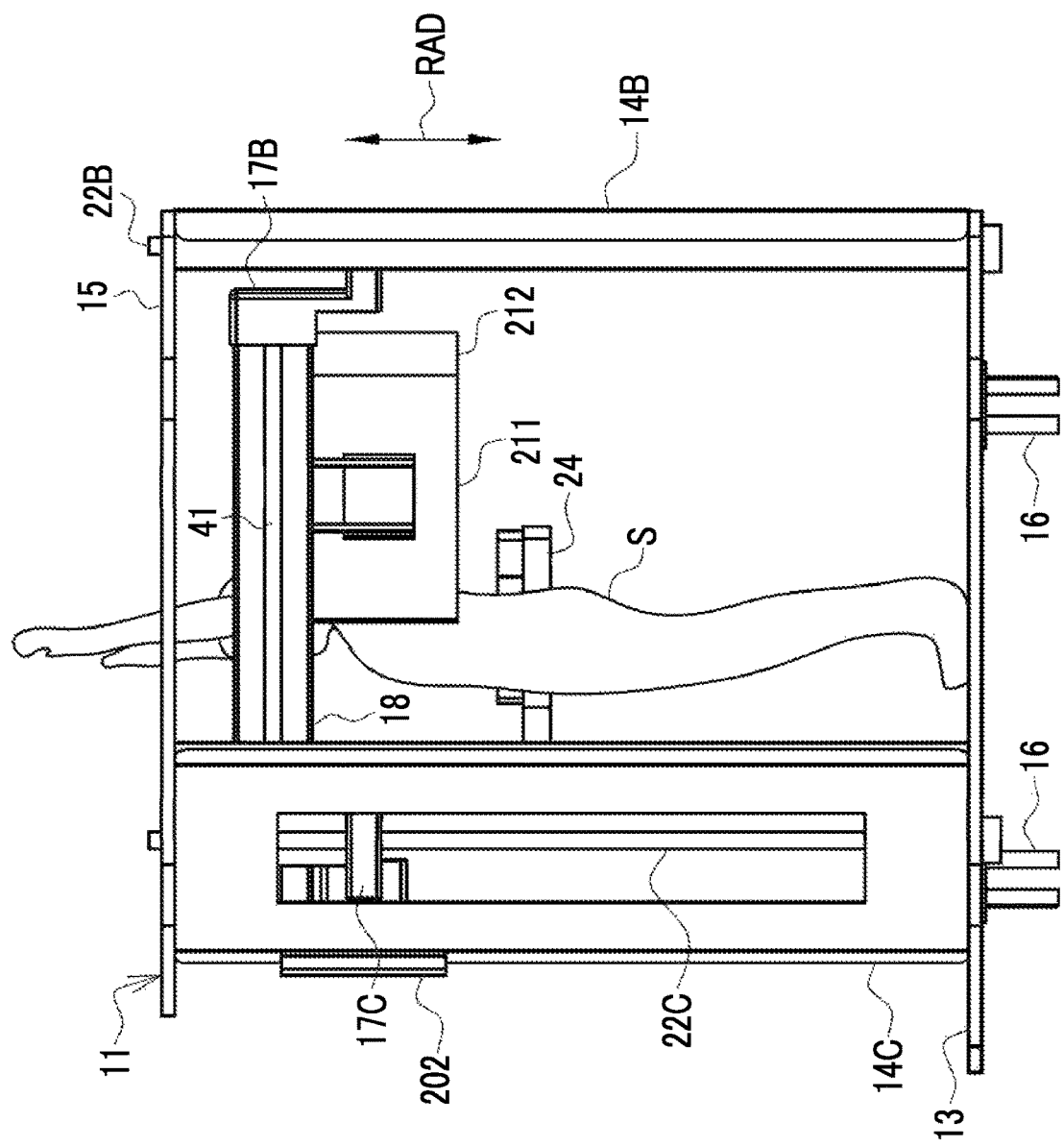
FIG. 2 is a side view illustrating the CT apparatus.

For example, as illustrated in FIG. 2, the apparatus main body 11 comprises a stage 13, three columns 14A, 14B, and 14C, and a top plate 15. The stage 13 is, for example, an octagonal flat plate (see FIG. 6). Casters 16 for transportation are attached to four corners of a rear surface of the stage 13. The caster 16 comprises a rotation lock mechanism (not illustrated). After the apparatus main body 11 is installed at an installation position, the rotation lock mechanism can be operated to lock the rotation of the caster 16. Alternatively, the caster 16 can be removed from the stage 13. The caster 16 can be removed after the apparatus main body 11 is installed at the installation position.

The outer shape of the columns 14A to 14C is a rectangular plate shape, and the columns 14A to 14C are vertically provided at four corners of the surface of the stage 13. The columns 14A and 14C are disposed on the front left and right sides of the apparatus main body 11 (the front left and right sides of the subject S). The column 14B is disposed at the center of the rear side of the apparatus main body 11 (behind the subject S). The top plate 15 is attached to the upper end portions of the columns 14A to 14C. The top plate 15 is, for example, an octagonal flat plate having an outer shape that follows the stage 13 (see FIG. 6). The top plate 15 has a C-shape in which a central portion is hollowed out in a circular shape and a portion corresponding to the front side of the apparatus main body 11 between the columns 14A and 14C is cut out. Further, in the following description, the columns 14A to 14C are collectively referred to as columns 14 in a case in which they do not need to be distinguished from each other.

A connection member 17A is connected to the column 14A, a connection member 17B is connected to the column 14B, and a connection member 17C is connected to the column 14C. A frame 18 is connected to the connection members 17A to 17C. That is, the columns 14A to 14C and the frame 18 are connected to each other through the connection members 17A to 17C. Furthermore, in the following description, the connection members 17A to 17C are collectively referred to as connection members 17 in a case in which they do not need to be distinguished from each other.

The frame 18 has an annular shape. The subject S is positioned at a center C (see FIG. 6) of the annular frame 18. FIGS. 1 and 2 illustrate an aspect in which the subject S in a standing posture with both hands raised above the head is positioned.

The column 14 is provided with a guide rail (not illustrated) to which the connection member 17 is fitted. The connection member 17 and thus the frame 18 can be raised and lowered in the vertical direction along the guide rail. That is, the columns 14 hold the frame 18 to be raised and lowered in the vertical direction. In addition, the frame 18 can be rotated around a body axis of the subject S, using an axis passing through the center C in the vertical direction as a rotation axis RA (see FIG. 3 and the like). That is, the columns 14A to 14C hold the frame 18 to be rotatable around the body axis of the subject S. Hereinafter, the center C may be referred to as a rotation center C. An arrow represented by letters RAD indicates a rotation axis direction of the frame 18. The rotation axis direction RAD is parallel to the vertical direction. Here, the body axis is an axis extending from the top of the head to a caudal portion (anus) of the subject S. In a case in which the subject S is in the standing posture or a sitting posture (see FIG. 4), the body axis is parallel to the vertical direction and the rotation axis direction RAD. The term "parallel" means parallel including an error which is generally allowed in the technical field to which the technology of the present disclosure belongs and is not contrary to the gist of the technology of the present disclosure, in addition to perfectly parallel. Further, the columns 14 may be expanded and contracted to change a height position of the frame 18.

A first radiation source 201 and a second radiation source 202 that irradiate the subject S with radiation R (see FIG. 7), such as X-rays or γ-rays, and a first radiation detector 211 and a second radiation detector 212 that detect the radiation R transmitted through the subject S are attached to the frame 18. The first radiation source 201 and the second radiation source 202 have a box shape, and the first radiation detector 211 and the second radiation detector 212 have a rectangular plate shape.

Figure 3:
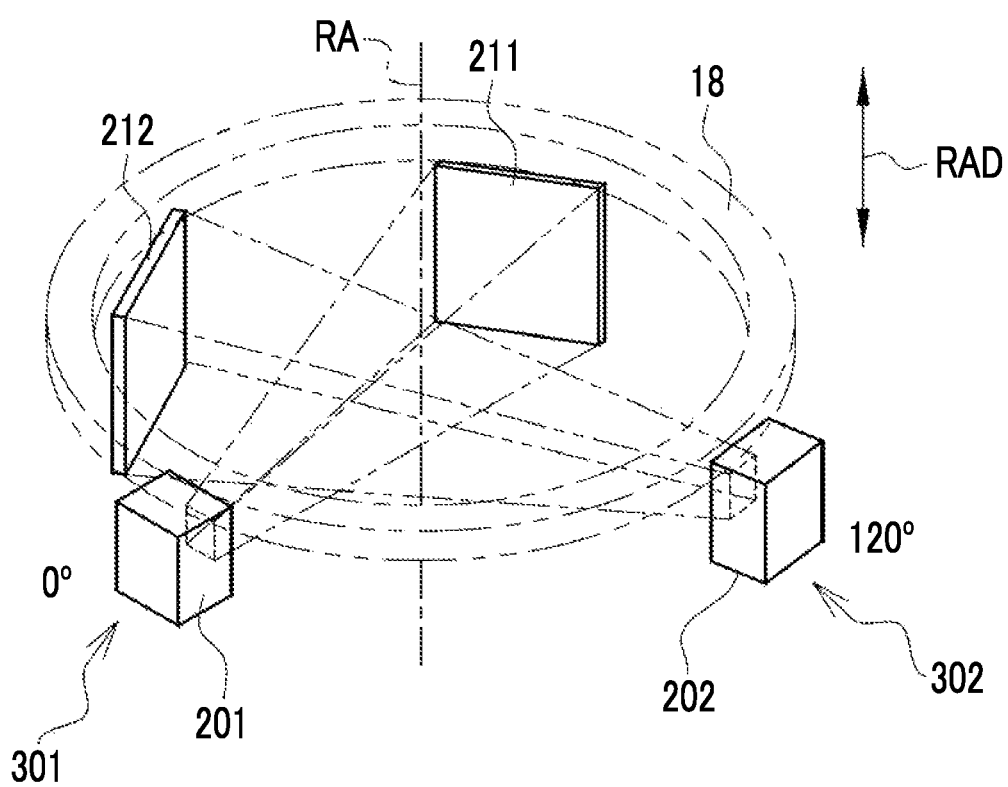
FIG. 3 is a diagram illustrating a configuration of a first imaging unit and a second imaging unit.

For example, as illustrated in FIG. 3, the first radiation source 201 and the first radiation detector 211 constitute a first imaging unit 301. In addition, the second radiation source 202 and the second radiation detector 212 constitute a second imaging unit 302. That is, the CT apparatus 10 has two imaging units of the first imaging unit 301 and the second imaging unit 302. Further, in the following description, the first radiation source 201 and the second radiation source 202 are collectively referred to as radiation sources 20 in a case in which they do not need to be distinguished from each other. In addition, the first radiation detector 211 and the second radiation detector 212 are collectively referred to as radiation detectors 21. Further, the first imaging unit 301 and the second imaging unit 302 are collectively referred to as imaging units 30.

Returning to FIGS. 1 and 2, the column 14A is provided with a screw shaft 22A, the column 14B is provided with a screw shaft 22B, and the column 14C is provided with a screw shaft 22C. The screw shafts 22A to 22C have a height from the stage 13 to the top plate 15. The screw shafts 22A to 22C are rotated to raise and lower the connection members 17A to 17C and thus the frame 18 in the rotation axis direction RAD. In addition, in the following description, the screw shafts 22A to 22C are collectively referred to as screw shafts 22 in a case in which they do not need to be distinguished from each other.

A touch panel display 25 is attached to the column 14A through a movable arm 24. The touch panel display 25 is operated by the operator. In addition, the touch panel display 25 displays various types of information to the operator.

Figure 4:
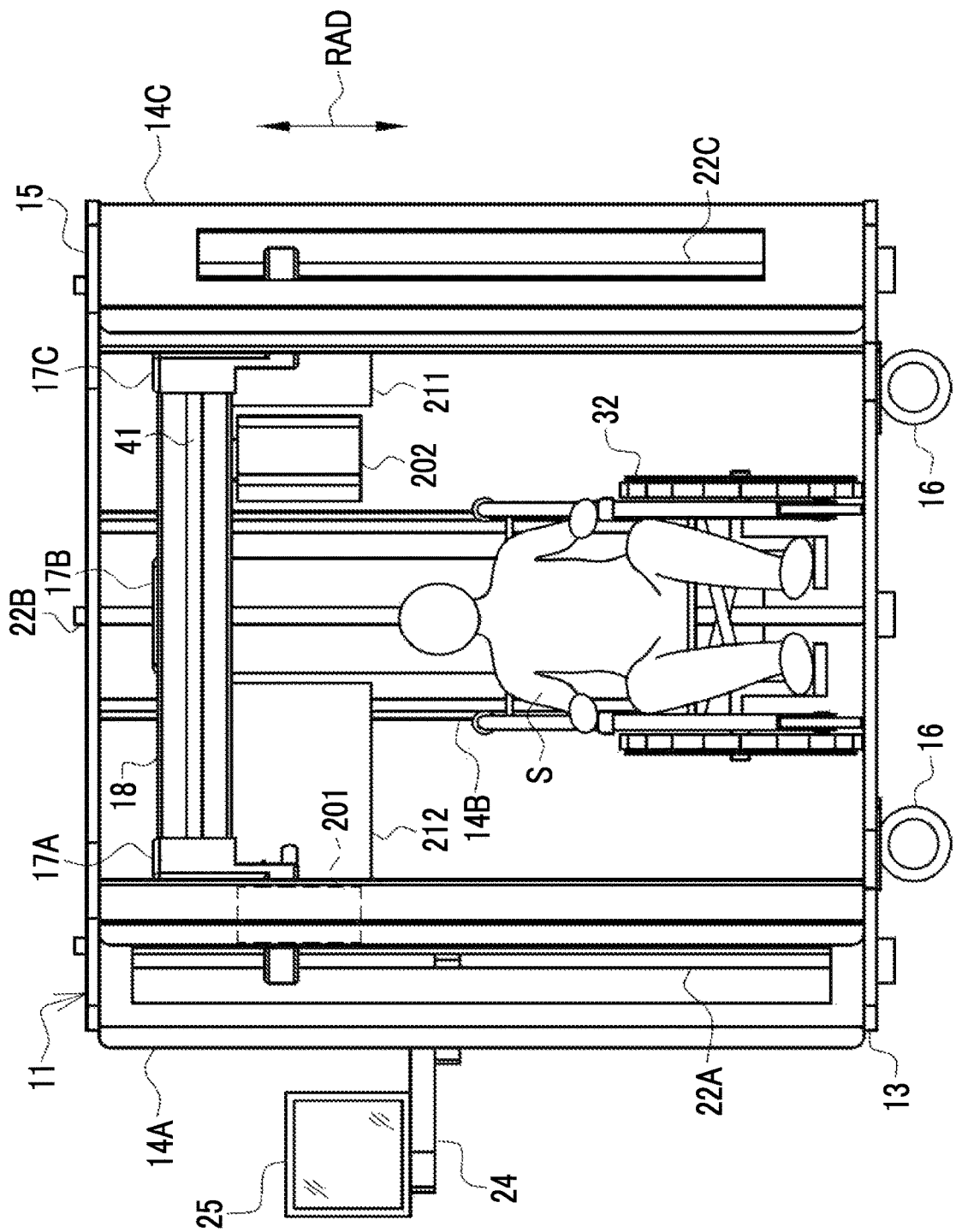
FIG. 4 is a front view illustrating the CT apparatus in a state in which a subject is positioned in a sitting posture on a wheelchair.

FIGS. 1 and 2 illustrate an example in which the subject S is positioned in the frame 18 in the standing posture with both hands raised above the head. However, the present disclosure is not limited thereto. For example, as illustrated in FIG. 4, the CT apparatus 10 can image the subject S who is positioned in the frame 18 in the sitting posture on a wheelchair 32. In addition, either the subject S in the standing posture or the subject S in the sitting posture on the wheelchair 32 is positioned such that the front side faces the columns 14A and 14C and the back side faces the column 14B.

Figure 5:
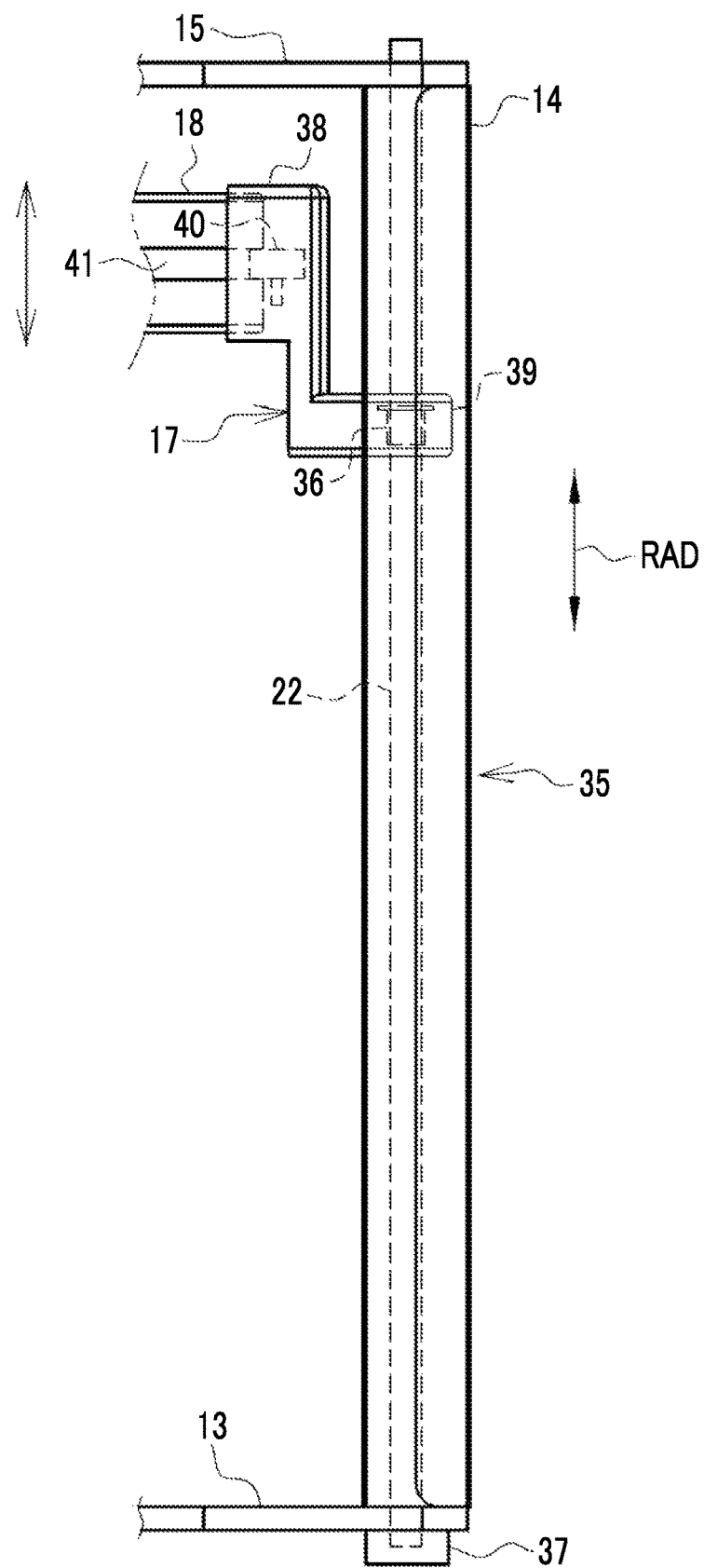
FIG. 5 is a diagram illustrating a frame elevating mechanism.

For example, as illustrated in FIG. 5, a frame elevating mechanism 35 that raises and lowers the connection member 17 and thus the frame 18 in the rotation axis direction RAD is a ball screw mechanism composed of the screw shaft 22, a nut 36 that has a ball provided therein and is engaged with the screw shaft 22, a frame elevating motor 37 that rotates the screw shaft 22, and the like. The frame elevating motor 37 is attached to the rear surface of the stage 13. The height position of the frame 18 is determined from the rotation direction and rotation speed of the frame elevating motor 37.

The connection member 17 has a first connection portion 38 that is connected to the frame 18 and a second connection portion 39 that is connected to the column 14. The first connection portion 38 protrudes toward the frame 18, and the second connection portion 39 protrudes toward the column 14. The connection member 17 has a Z-shape as a whole. A bearing 40 is provided in the first connection portion 38. The bearing 40 is fitted to a guide groove 41 (see also FIG. 1 and the like) that is formed over the entire circumference of the frame 18. The bearing 40 rolls as the frame 18 is rotated. The nut 36 is provided in the second connection portion 39.

Figure 6:
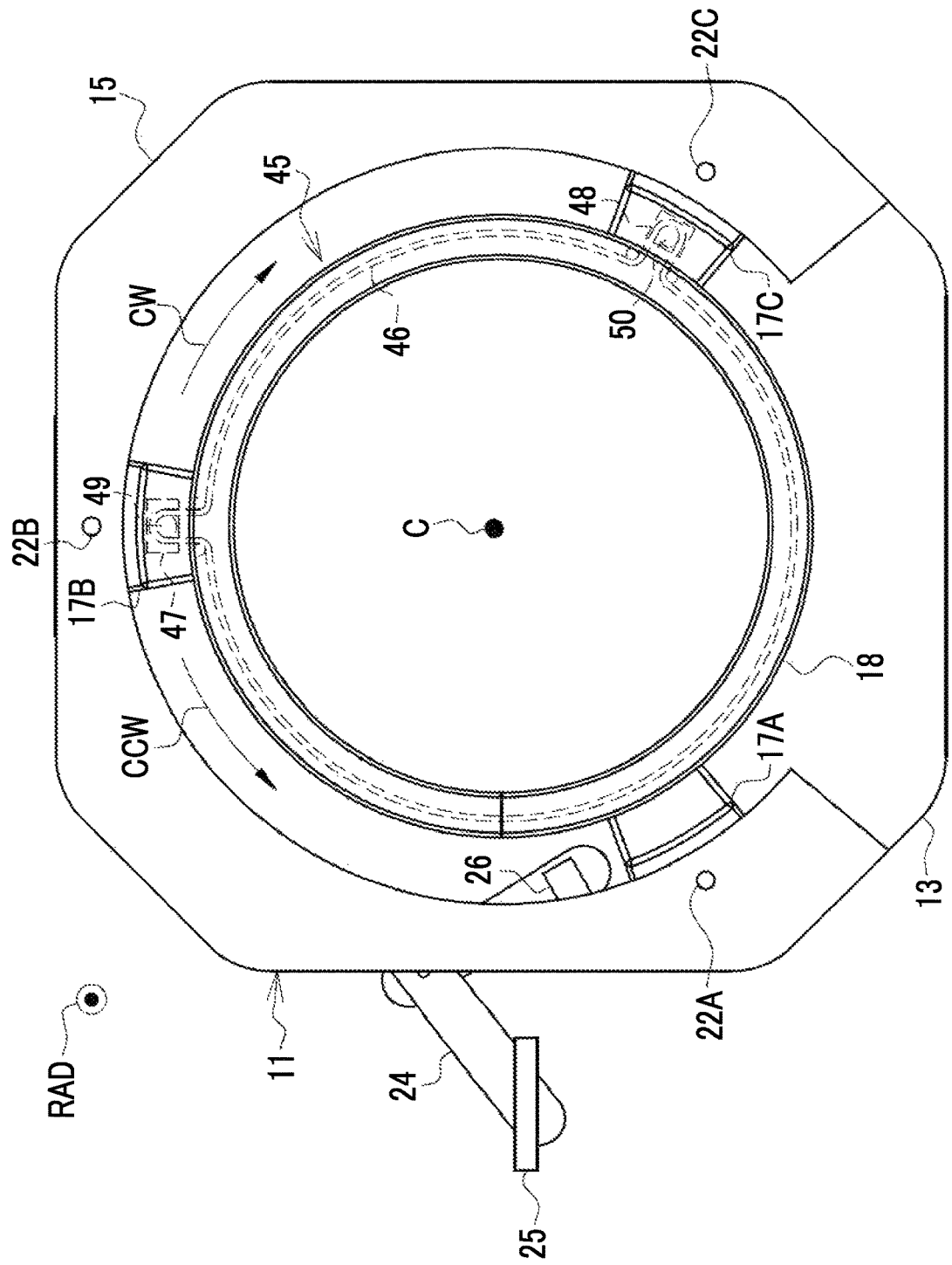
FIG. 6 is a diagram illustrating a rotation mechanism.

For example, as illustrated in FIG. 6, a rotation mechanism 45 that rotates the frame 18 and thus the imaging unit 30 around the body axis of the subject S is composed of a rotation belt 46 that is wound around the entire circumference of the frame 18, a rotary motor 47, a potentiometer 48, and the like. The rotary motor 47 is provided in the connection member 17B and is connected to a portion of the rotation belt 46 drawn out from the frame 18 through a pulley 49. The rotary motor 47 is driven to rotate the frame 18 and thus the imaging unit 30 in a clockwise (right-hand rotation) direction CW and a counterclockwise (left-hand rotation) direction CCW. The clockwise direction CW and the counterclockwise direction CCW are examples of a "rotation direction" according to the technology of the present disclosure.

The potentiometer 48 is provided in the connection member 17C and is connected to a portion of the rotation belt 46 drawn out from the frame 18 through a pulley 50. The potentiometer 48 has a variable resistor whose resistance value is changed depending on the rotation position of the frame 18 and outputs a voltage signal corresponding to the rotation position of the frame 18. The rotation position of the frame 18 is determined by the voltage signal from the potentiometer 48. In addition, in FIG. 6, the imaging unit 30 is not illustrated in order to avoid complication.

Figure 7:
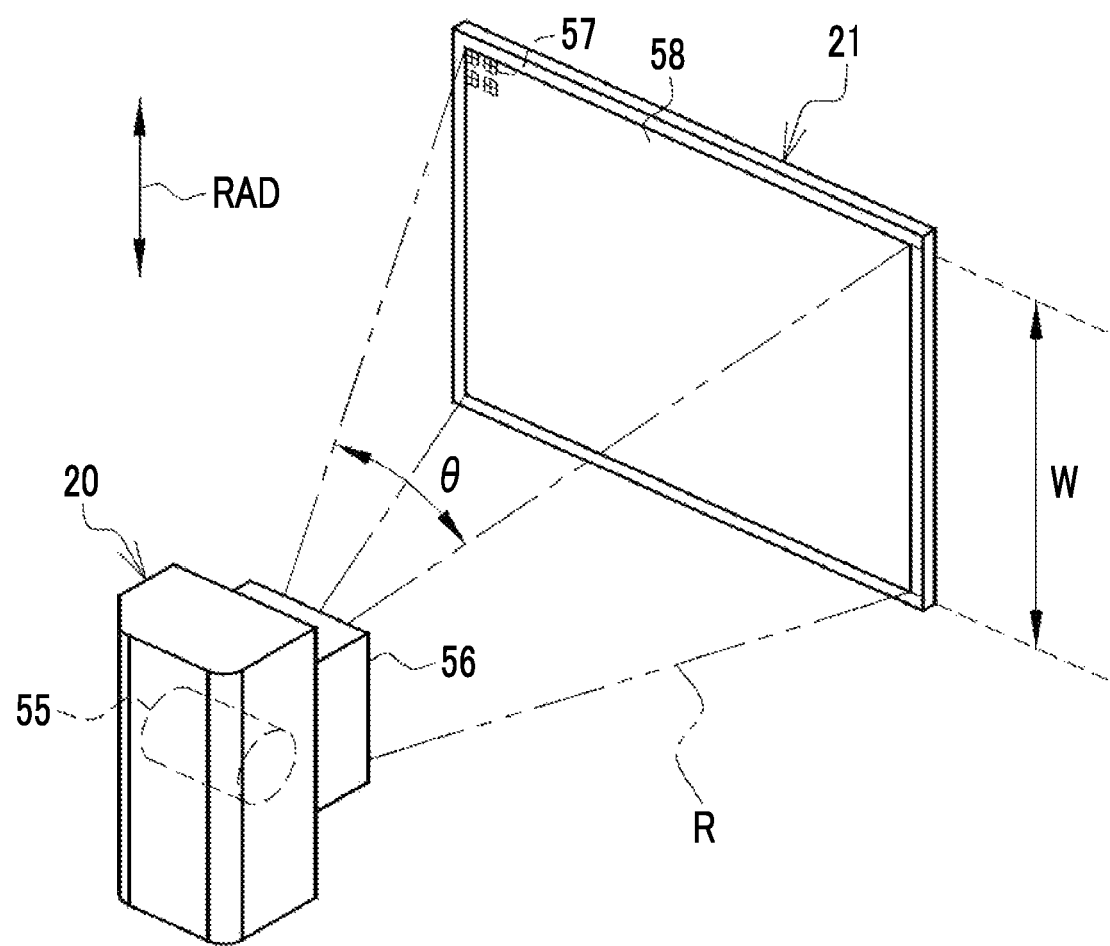
FIG. 7 is a perspective view illustrating a radiation source, a radiation detector, and radiation.

For example, as illustrated in FIG. 7, the radiation source 20 includes a radiation tube 55. The radiation tube 55 emits the radiation R. In addition, the radiation source 20 is also provided with an irradiation field lamp that emits, for example, orange visible light indicating an irradiation field of the radiation R, which is not illustrated.

The radiation source 20 has an irradiation field limiter 56. The irradiation field limiter 56 is also called a collimator and defines the irradiation field of the radiation R to the radiation detector 21. An incident opening through which the radiation R from the radiation tube 55 is incident and an exit opening through which the radiation R exits are formed in the irradiation field limiter 56. For example, four shielding plates are provided in the vicinity of the exit opening. The shielding plate is made of a material that shields the radiation R, for example, lead. The shielding plates are disposed on each side of a quadrangle, in other words, are assembled in a checkered pattern and form a quadrangular irradiation opening through which the radiation R is transmitted. The irradiation field limiter 56 changes the position of each shielding plate to change the size of the irradiation opening, thereby changing the irradiation field of the radiation R to the radiation detector 21. The radiation R having a quadrangular pyramid shape is emitted from the radiation source 20 by the operation of the irradiation field limiter 56. An emission angle θ of the radiation R as viewed from the rotation axis direction RAD is, for example, 10° to 30°. The emission angle θ is also called a cone angle.

The radiation detector 21 is composed of, for example, a scintillator that converts the radiation R into visible light, a thin film transistor (TFT) substrate having a detection surface 58 in which a plurality of pixels 57 that accumulate charge corresponding to the visible light to detect the radiation R are arranged in a two-dimensional matrix, a signal processing circuit that outputs a voltage signal corresponding to the charge as a projection image, and a housing that accommodates these components. The detection surface 58 has a size of, for example, 430 mm×430 mm (17 inches). Letter W indicates the width of the detection surface 58 in the rotation axis direction RAD. A source-to-image distance (SID) which is a distance from the focus of the radiation R (a point at which the radiation R is emitted in the radiation tube 55) to the detection surface 58 is, for example, 1200 mm. In addition, the radiation detector 21 may be a type that directly detects the radiation R instead of the visible light converted from the radiation R.

Figure 8:
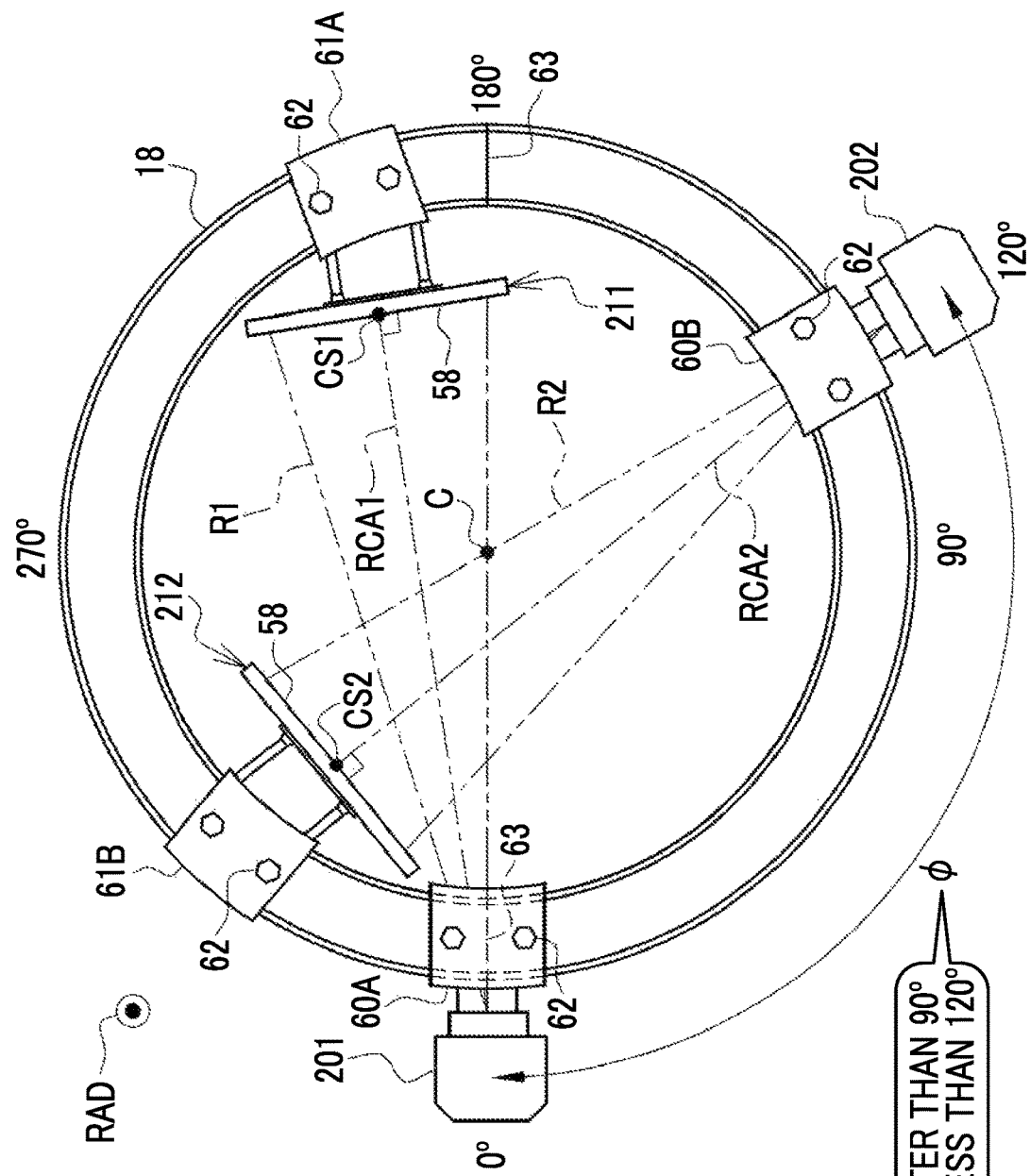
FIG. 8 is a diagram illustrating positions where a first imaging unit and a second imaging unit are disposed.

For example, as illustrated in FIG. 8, in a case in which the position where the first radiation source 201 is disposed is 0° and the positions of every 90° in the counterclockwise direction CCW are 90°, 180°, and 270° as viewed from the rotation axis direction RAD, the second radiation source 202 is disposed at a position that is separated from the first radiation source 201 by an angle φ that is equal to or greater than 90° and equal to or less than 120°. The first radiation detector 211 and the second radiation detector 212 are disposed at positions corresponding to the positions where the first radiation source 201 and the second radiation source 202 are disposed. Therefore, the first imaging unit 301 and the second imaging unit 302 have different phases in the rotation direction. In addition, in this example, φ is 120°.

First radiation R1 which is the radiation R from the first radiation source 201 and second radiation R2 which is the radiation R from the second radiation source 202 intersect with each other in the vicinity of the rotation center C of the frame 18. A first central axis RCA1 of a flux of the first radiation R1 perpendicularly intersects a first center point CS1 of the detection surface 58 of the first radiation detector 211. Similarly, a second central axis RCA2 of a flux of the second radiation R2 perpendicularly intersects a second center point CS2 of the detection surface 58 of the second radiation detector 212. Further, in the following description, the first central axis RCA1 and the second central axis RCA2 are collectively referred to as central axes RCA in a case in which they do not need to be distinguished from each other. In addition, the first center point CS1 and the second center point CS2 are collectively referred to as center points CS.

The first radiation source 201 and the second radiation source 202 are attached to the frame 18 by attachments 60A and 60B, respectively. Similarly, the first radiation detector 211 and the second radiation detector 212 are attached to the frame 18 by attachments 61A and 61B, respectively. The attachments 60A, 60B, 61A, and 61B are fixed to the frame 18 by bolts 62. Therefore, the first imaging unit 301 and the second imaging unit 302 are rotated together in the same rotation direction by the rotation mechanism 45 while maintaining the positional relationship therebetween. The radiation source 20 is disposed outside the frame 18, and the radiation detector 21 is disposed inside the frame 18 as viewed from the rotation axis direction RAD.

The frame 18 is formed by joining two semi-annular members by, for example, welding. The attachment 60A is attached to cover one of two opposing joint portions 63 of the frame 18. This attachment of the attachment 60A to the joint portion 63 makes it possible to reinforce the joint portion 63, which is a mechanically weak portion, with the attachment 60A.

Figure 9:
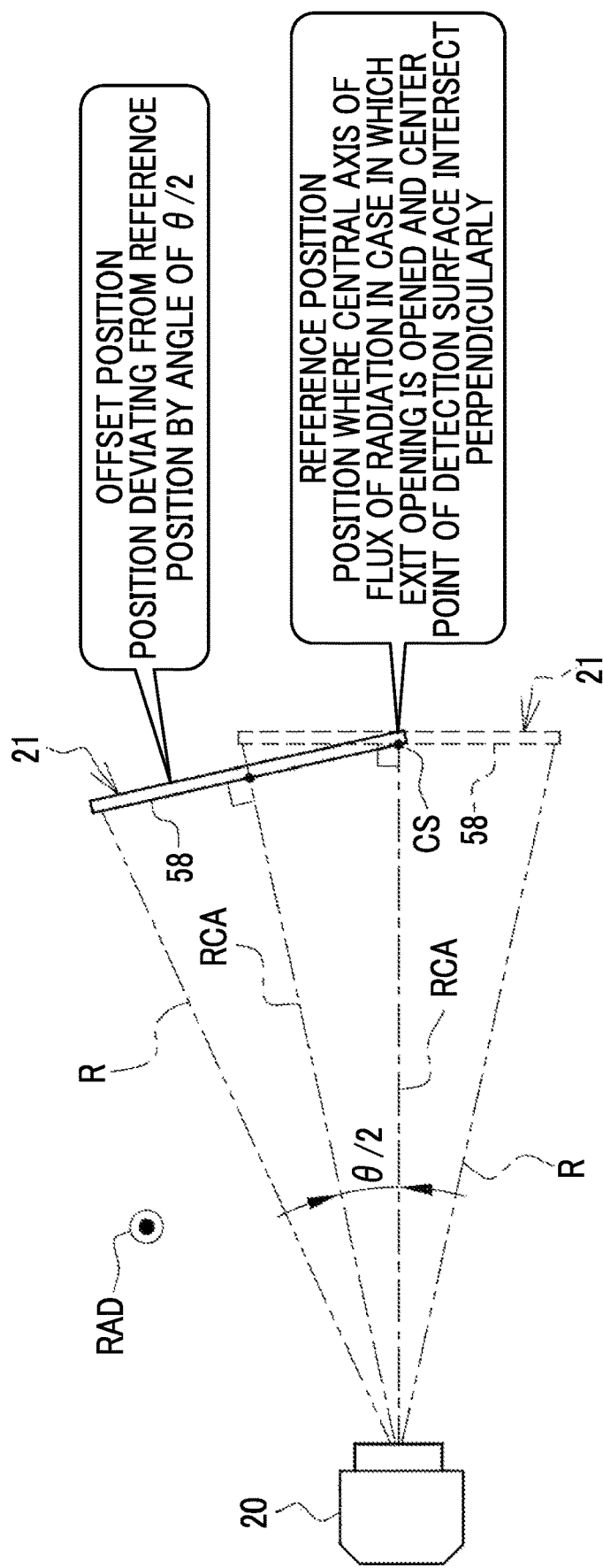
FIG. 9 is a diagram illustrating a reference position and an offset position of the radiation detector.

For example, as illustrated in FIG. 9, the radiation detector 21 is disposed at an offset position that is separated from a reference position facing the radiation source 20 by a preset angle as viewed from the rotation axis direction RAD. Here, the reference position is a position where the central axis RCA of the flux of the radiation R in a case in which the exit opening of the irradiation field limiter 56 is opened to the maximum and the center point CS of the detection surface 58 of the radiation detector 21 intersect perpendicularly. The preset angle at the offset position is half (θ/2) of the emission angle θ in this example.

Figure 10:
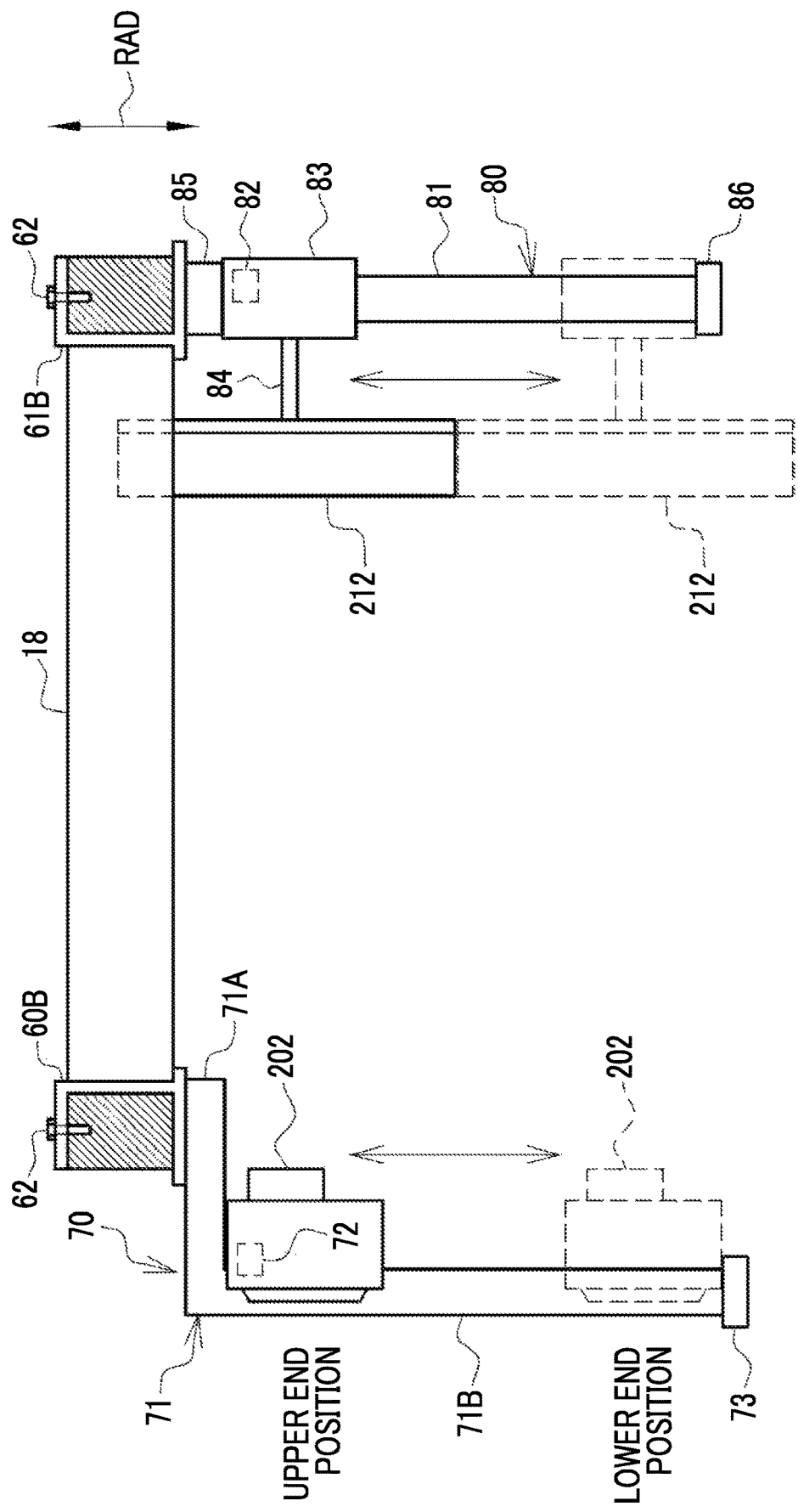
FIG. 10 is a diagram illustrating a radiation source elevating mechanism and a detector elevating mechanism.

For example, as illustrated in FIG. 10, the second radiation source 202 is raised and lowered in the rotation axis direction RAD by a radiation source elevating mechanism 70. The radiation source elevating mechanism 70 is composed of, for example, a guide rail 71 and a radiation source elevating motor 72. The guide rail 71 is composed of a first portion 71A that extends from the attachment 60B to the outside of the frame 18 and a second portion 71B that is bent at a right angle from the first portion 71A and extends downward along the rotation axis direction RAD. The second portion 71B has a length capable of covering the half body (the upper half of the body above the waist and the lower half of the body below the waist) of a general adult male. Here, the "length capable of covering the half body of the general adult male" is, for example, a length of about 100 cm in a case in which 200 cm is considered as the maximum height although there is a race or individual difference. This setting of the length of the second portion 71B to the "length capable of covering the half body of the general adult male" makes it possible to perform imaging and diagnosis without omitting the entire half body. It is possible to reduce a concern that re-imaging will be required due to the omission of imaging, which causes an increase in imaging time and an increase in the radiation exposure of the subject S. In consideration of a case in which the whole body of the subject S is imaged instead of the half body, the length of the second portion 71B may be set to be greater than about 100 cm. In addition, in FIG. 10, the first radiation source 201 and the first radiation detector 211 are not illustrated in order to avoid complication.

The second radiation source 202 is attached to the second portion 71B. The raising of the second radiation source 202 is regulated by the first portion 71A. In addition, a stopper 73 is provided at a lower end of the second portion 71B. The lowering of the second radiation source 202 is regulated by the stopper 73. The second radiation source 202 can be raised and lowered between an upper end position determined by the first portion 71A and a lower end position determined by the stopper 73.

The radiation source elevating motor 72 is rotationally driven to move the second radiation source 202 along the second portion 71B. The height position of the second radiation source 202 is determined from the rotation direction and rotation speed of the radiation source elevating motor 72. In addition, the radiation source elevating motor 72 is an example of an "electric actuator" according to the technology of the present disclosure.

The second radiation detector 212 is raised and lowered in the rotation axis direction RAD by a detector elevating mechanism 80. The detector elevating mechanism 80 is composed of, for example, a guide rail 81 and a detector elevating motor 82. The guide rail 81 extends straight downward from the attachment 61B along the rotation axis direction RAD. The guide rail 81 has a length capable of covering the half body of the general adult male, similarly to the second portion 71B of the guide rail 71.

An elevating box 83 is attached to the guide rail 81. The detector elevating motor 82 is provided in the elevating box 83. The second radiation detector 212 is attached to the elevating box 83 through an arm 84 (see also FIG. 8). The arm 84 is an elongated rod that extends from a central portion of the elevating box 83 to the inside of the frame 18.

Stoppers 85 and 86 are provided at upper and lower ends of the guide rail 81, respectively. The raising of the second radiation detector 212 is regulated by the stopper 85, and the lowering of the second radiation detector 212 is regulated by the stopper 86. The second radiation detector 212 can be raised and lowered between an upper end position determined by the stopper 85 and a lower end position determined by the stopper 86. The upper end position and the lower end position of the second radiation detector 212 correspond to the upper end position and the lower end position of the second radiation source 202, respectively.

The detector elevating motor 82 is rotationally driven in operative association with the radiation source elevating motor 72 to move the elevating box 83 and thus the second radiation detector 212 along the guide rail 81. The height position of the second radiation detector 212 is determined from the rotation direction and rotation speed of the detector elevating motor 82. In addition, the detector elevating motor 82 is an example of the "electric actuator" according to the technology of the present disclosure, similarly to the radiation source elevating motor 72.

The radiation source elevating mechanism 70 and the detector elevating mechanism 80 are not provided in the first radiation source 201 and the first radiation detector 211 which are not illustrated in FIG. 10. Therefore, the first radiation source 201 and the first radiation detector 211 are not raised and lowered in the rotation axis direction RAD. The height positions of the first radiation source 201 and the first radiation detector 211 are fixed to the upper end positions (see FIGS. 11 and 12).

While the height positions of the first radiation source 201 and the first radiation detector 211 are fixed to the upper end positions, the height positions of the second radiation source 202 and the second radiation detector 212 are changed by the radiation source elevating mechanism 70 and the detector elevating mechanism 80, respectively. That is, an interval between the first imaging unit 301 and the second imaging unit 302 in the rotation axis direction RAD changes. Therefore, the CT apparatus 10 can perform imaging with a relatively large interval between the first imaging unit 301 and the second imaging unit 302 in the rotation axis direction RAD or can perform imaging with a relatively small interval between the first imaging unit 301 and the second imaging unit 302 in the rotation axis direction RAD. The radiation source elevating mechanism 70 and the detector elevating mechanism 80 are examples of a "displacement mechanism" according to the technology of the present disclosure.

Figure 11:
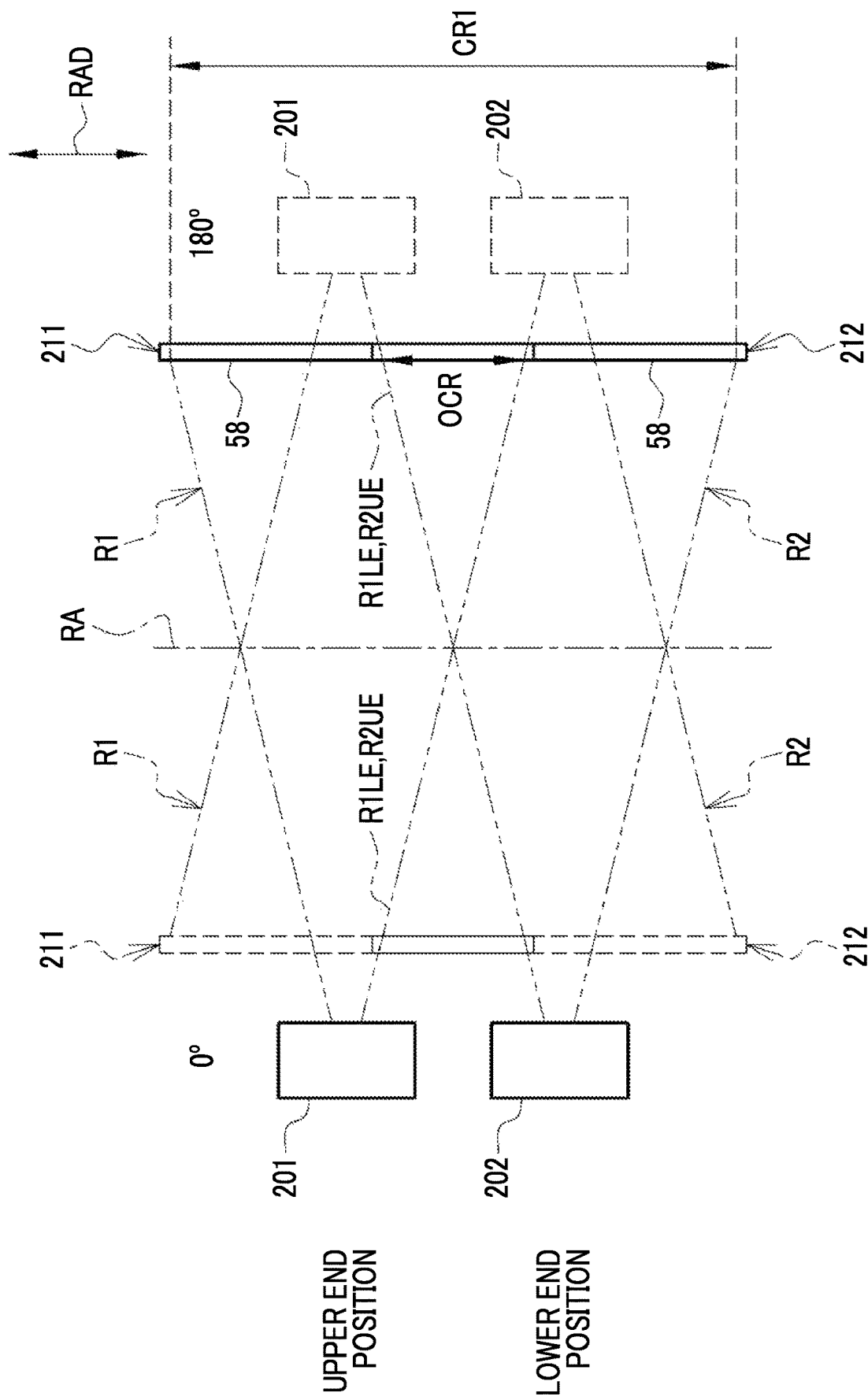
FIG. 11 is a diagram illustrating a flux of radiation in a case in which the first imaging unit is located at an upper end position and the second imaging unit is located at a lower end position.

For example, as illustrated in FIG. 11, in a case in which the second radiation source 202 and the second radiation detector 212 are located at the lower end positions, a lower end RILE of the flux of the first radiation R1 is matched with an upper end R2UE of the flux of the second radiation R2. In other words, the upper end position and the lower end position in this example are positions where the lower end RILE of the flux of the first radiation R1 is matched with the upper end R2UE of the flux of the second radiation R2. A first imaging range CR1, which is an imaging range in this case, is a range having a width that is about 1.5 times the width W of the detection surface 58 of one radiation detector 21 in the rotation axis direction RAD. That is, the first imaging range CR1 is a range that exceeds the width W. In addition, FIG. 11 illustrates the radiation R in a case in which the radiation source 20 and the radiation detector 21 are located at each of the positions of 0° and 180° illustrated in FIG. 8 for convenience of explanation. Further, in FIG. 11, the radiation detector 21 is not offset unlike FIG. 9 in order to avoid complication. The same is applied to FIG. 12 and the like which will be described below.

The first imaging unit 301 and the second imaging unit 302 have an overlapping imaging range as represented by letters OCR. An imaging control unit 112 disposes the first imaging unit 301 and the second imaging unit 302 at the positions where the overlapping imaging ranges OCR can be secured. That is, the imaging control unit 112 sets the interval between the first imaging unit 301 and the second imaging unit 302 in the rotation axis direction RAD such that the overlapping imaging range OCR occurs between a first projection image 311 and a second projection image 312 (see FIG. 16) obtained from the first imaging unit 301 and the second imaging unit 302, respectively.

Figure 12:
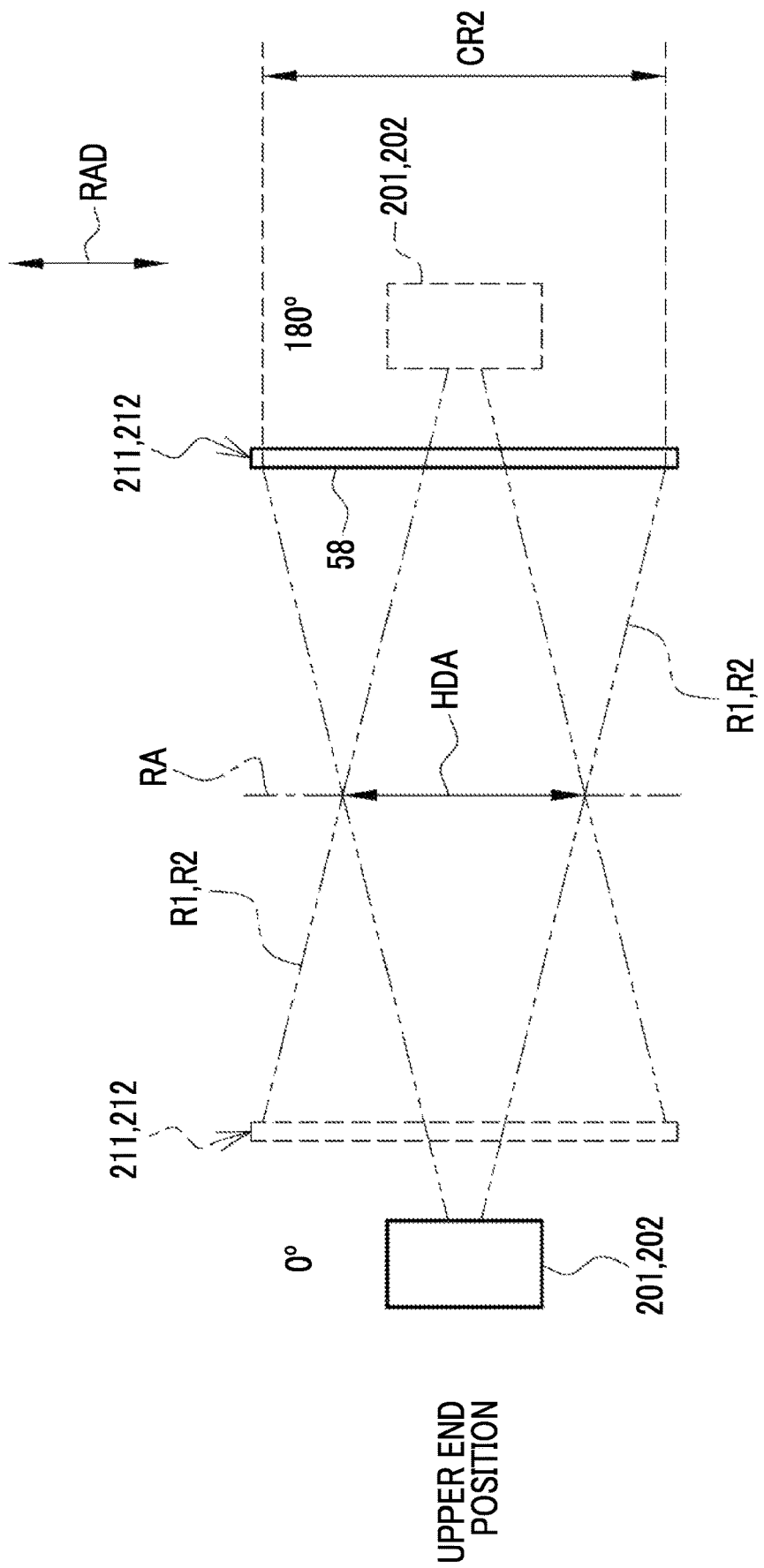
FIG. 12 is a diagram illustrating a flux of radiation in a case in which both the first imaging unit and the second imaging unit are located at the upper end positions.

For example, as illustrated in FIG. 12, in a case in which the second radiation source 202 and the second radiation detector 212 are located at the upper end positions, the flux of the first radiation R1 is matched with the flux of the second radiation R2. A second imaging range CR2, which is an imaging range in this case, is a range that is matched with the width W of the detection surface 58 of one radiation detector 21 in the rotation axis direction RAD. That is, the second imaging range CR2 is a range within the width W. A region which is represented by an arrow and letters HDA and which is irradiated with the first radiation R1 and the second radiation R2 at any rotation angle is a region in which a high-definition tomographic image can be obtained (hereinafter, referred to as a high-definition drawing region). The width of the high-definition drawing region HDA in the rotation axis direction RAD is, for example, 200 mm to 300 mm. Further, in this embodiment, the term "match" means match including an error that is generally allowed in the technical field to which the technology of the present disclosure belongs and does not deviate from the gist of the technology of the present disclosure, in addition to perfect match.

The aspect illustrated in FIG. 11 is an example of the imaging in which the interval between the first imaging unit 301 and the second imaging unit 302 in the rotation axis direction RAD is relatively large. On the other hand, the aspect illustrated in FIG. 12 is an example of the imaging in which the interval between the first imaging unit 301 and the second imaging unit 302 in the rotation axis direction RAD is relatively small.

Figure 13:
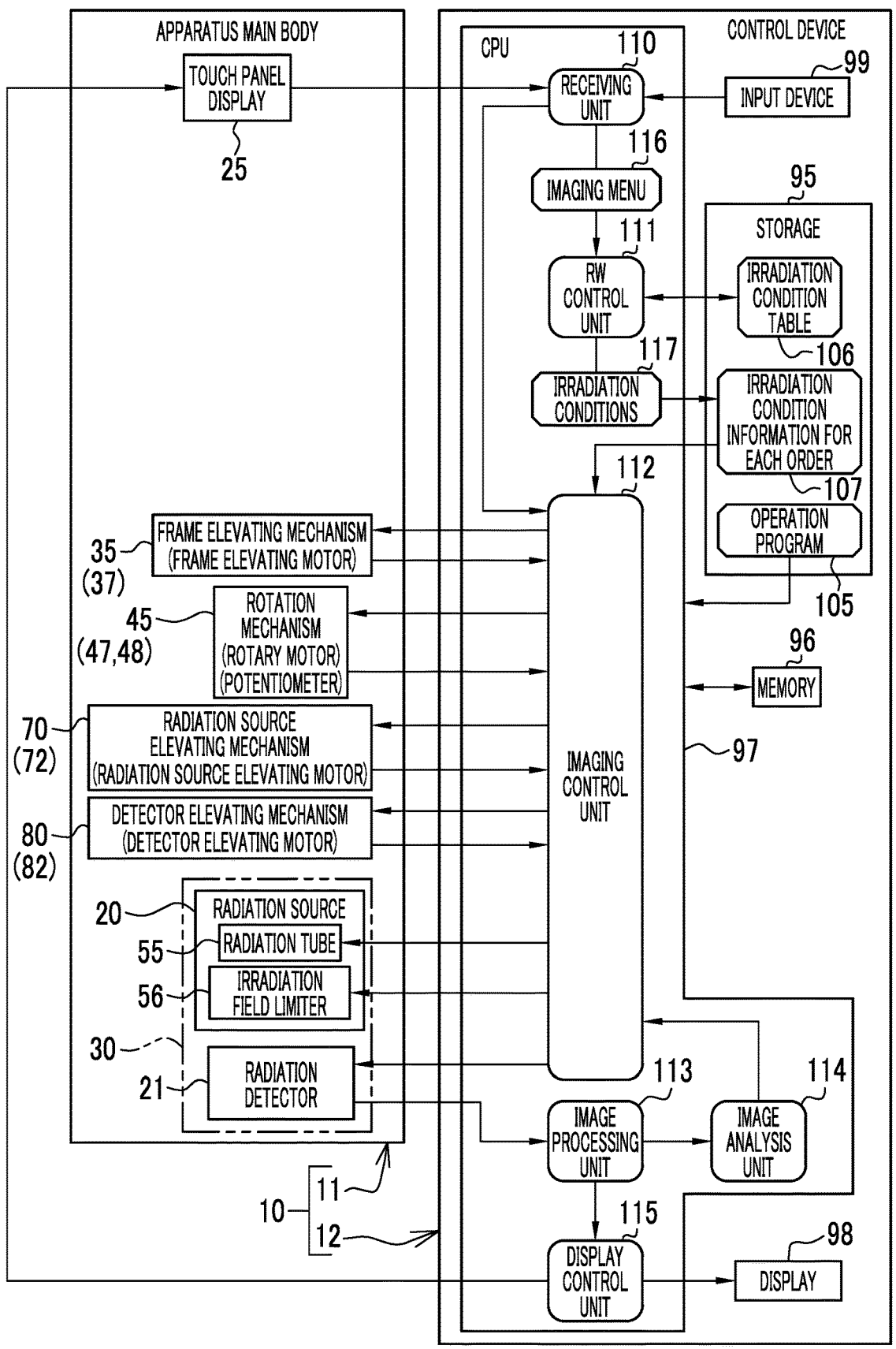
FIG. 13 is a block diagram illustrating a processing unit of a CPU of a control device.

For example, as illustrated in FIG. 13, a computer constituting the control device 12 comprises a storage 95, a memory 96, a central processing unit (CPU) 97, a display 98, an input device 99, and the like.

The storage 95 is a hard disk drive that is provided in the computer constituting the control device 12 or that is connected to the computer through a cable or a network. Alternatively, the storage 95 is a disk array in which a plurality of hard disk drives are connected. The storage 95 stores, for example, a control program, such as an operating system, various application programs, and various types of data associated with these programs. In addition, a solid state drive may be used instead of the hard disk drive.

The memory 96 is a work memory for the CPU 97 to perform processes. The CPU 97 loads the program stored in the storage 95 to the memory 96 and performs a process corresponding to the program. Therefore, the CPU 97 controls the overall operation of each unit of the computer. The CPU 97 is an example of a "processor" according to the technology of the present disclosure. In addition, the memory 96 may be provided in the CPU 97.

The display 98 displays various screens. The various screens have operation functions by a graphical user interface (GUI). The computer constituting the control device 12 receives operation instructions input from the input device 99 through various screens. The input device 99 is, for example, a keyboard, a mouse, a touch panel, a microphone for voice input.

An operation program 105 is stored in the storage 95. The operation program 105 is an application program for causing the computer to function as the control device 12. The storage 95 stores, for example, an irradiation condition table 106 and irradiation condition information 107 for each order, in addition to the operation program 105.

In a case in which the operation program 105 is started, the CPU 97 of the control device 12 functions as a receiving unit 110, a read and write (hereinafter, abbreviated to RW) control unit 111, the imaging control unit 112, an image processing unit 113, an image analysis unit 114, and a display control unit 115 in cooperation with, for example, the memory 96.

The receiving unit 110 receives various operation instructions input by the operator through the touch panel display 25 of the apparatus main body 11 and the input device 99. For example, the receiving unit 110 receives an imaging menu 116. The receiving unit 110 outputs the imaging menu 116 to the RW control unit 111.

The RW control unit 111 receives the imaging menu 116 from the receiving unit 110. The RW control unit 111 reads irradiation conditions 117 of the radiation R which correspond to the received imaging menu 116 from the irradiation condition table 106. The RW control unit 111 writes the irradiation conditions 117 read from the irradiation condition table 106 to the irradiation condition information 107 for each order.

The imaging control unit 112 controls the operations of the radiation source 20 (the radiation tube 55 and the irradiation field limiter 56), the frame elevating mechanism 35 (frame elevating motor 37), and the rotation mechanism 45 (the rotary motor 47 and the potentiometer 48). In addition, the imaging control unit 112 controls the operations of the radiation source elevating mechanism 70 (radiation source elevating motor 72), the detector elevating mechanism 80 (detector elevating motor 82), and the radiation detector 21. The imaging control unit 112 reads the irradiation conditions 117 from the irradiation condition information 107 for each order. The imaging control unit 112 drives the irradiation field limiter 56 according to the irradiation conditions 117 to adjust the irradiation field. The operator inputs an imaging instruction to the control device 12 through an irradiation switch (not illustrated). In a case in which the imaging instruction is input, the imaging control unit 112 drives the radiation tube 55 according to the irradiation conditions 117 such that the radiation tube 55 generates the radiation R. The imaging control unit 112 outputs a projection image obtained by the detection of the emitted radiation R by the radiation detector 21 from the radiation detector 21 to the image processing unit 113.

The image processing unit 113 receives the projection image from the radiation detector 21. The image processing unit 113 performs various types of image processing on the projection image. Further, the image processing unit 113 performs a reconstruction process on a plurality of projection images subjected to the image processing to generate tomographic images. The image processing unit 113 outputs the tomographic images to the image analysis unit 114 and the display control unit 115.

The image analysis unit 114 performs an image analysis process on the tomographic image to specify a suspected part in the tomographic image. The suspected part is a part that is considered to be the cause of a disease and is, for example, a part in which a nerve is narrowed in the spine. The image analysis process is a so-called computer-aided diagnosis (CAD) process. The image analysis unit 114 outputs height position information of the specified suspected part to the imaging control unit 112.

The display control unit 115 controls the display of various types of information on the touch panel display 25 and the display 98. The display control unit 115 receives the tomographic image from the image processing unit 113. The display control unit 115 displays the tomographic image on the touch panel display 25 and the display 98.

The imaging menu 116 includes, for example, imaging order identification data (ID) and an imaging technique. The imaging order ID is identification information of an imaging order issued by a doctor who makes a diagnosis using the tomographic image. The imaging technique is composed of a posture of the subject S, such as a standing posture or a sitting posture, an imaging part, such as the head, the neck, or the entire spine, and attributes of the subject S such as an adult male, an adult female, and a child.

The imaging order is transmitted from a radiology information system (RIS) (not illustrated) to the control device 12. The control device 12 displays a list of the imaging orders on the display 98 under the control of the display control unit 115. The operator browses the list of the imaging orders and checks the content of the list. Then, the control device 12 displays the imaging menu corresponding to the imaging order on the display 98 such that it can be set. The operator operates the input device 99 to select the imaging menu corresponding to the imaging order and to input the imaging menu.

The irradiation conditions 117 are registered in the irradiation condition table 106 for each imaging technique. The irradiation conditions 117 include a tube voltage and a tube current applied to the radiation tube 55 and the irradiation time of the radiation R. In addition, the irradiation conditions 117 also include the size of the irradiation field. The operator can finely adjust the irradiation conditions 117 by hand. Further, instead of the tube current and the irradiation time, a tube current-irradiation time product, that is, a so-called mAs value may be set as the irradiation condition 117.

The irradiation conditions 117 for each imaging order ID are registered in the irradiation condition information 107 for each order. The imaging control unit 112 reads the irradiation conditions 117 corresponding to an imaging order ID of the next imaging from the irradiation condition information 107 for each order and controls the operation of each unit according to the read irradiation conditions 117.

Figure 14:
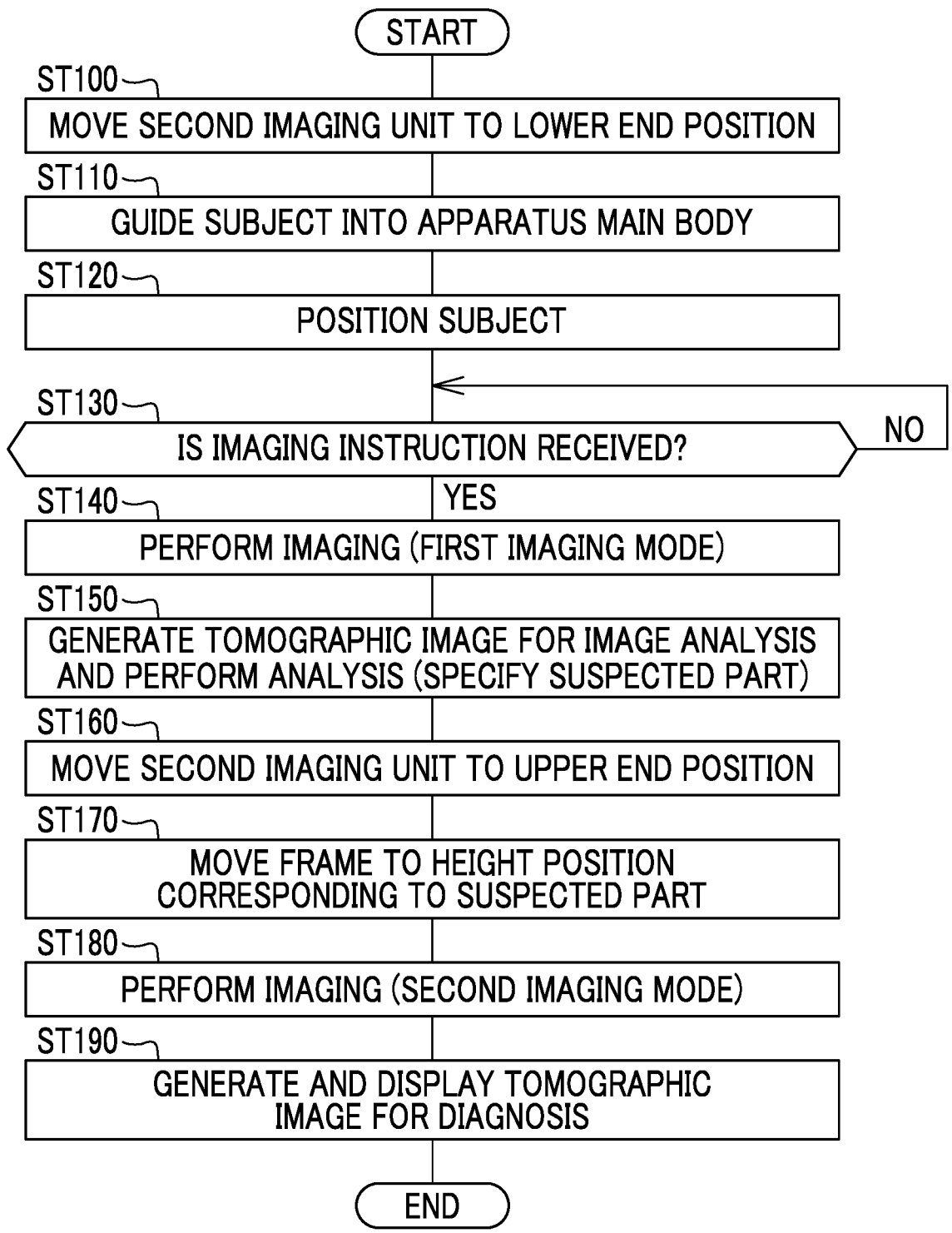
FIG. 14 is a flowchart illustrating an imaging procedure by the CT apparatus.

Next, an example of an imaging procedure by the CT apparatus 10 will be described with reference to a flowchart illustrated in FIG. 14. First, the frame elevating mechanism 35 is operated under the control of the imaging control unit 112 to move the frame 18 to a height position corresponding to the imaging menu 116. For example, in the case of the imaging menu 116 indicating the imaging of the entire spine of the subject S who is an adult male, the frame 18 is moved to a height position corresponding to the head of the subject S. In addition, as illustrated in FIG. 11, the radiation source elevating mechanism 70 and the detector elevating mechanism 80 are operated under the control of the imaging control unit 112 to move the second radiation source 202 and the second radiation detector 212 (second imaging unit 302) to the lower end position, respectively (Step ST100). Further, the irradiation field limiter 56 is operated under the control of the imaging control unit 112 to adjust the irradiation field to an irradiation field corresponding to the irradiation conditions 117.

Then, the subject S is guided into the apparatus main body 11 by the operator (Step ST110), and the subject S is positioned by the operator (Step ST120). In this case, an irradiation field lamp that is provided in the radiation source 20 is turned on as necessary, and the operator determines whether or not the height position of the frame 18 and the positioning of the subject S are appropriate for imaging. In a case in which the height position of the frame 18 and the positioning of the subject S are not appropriate for imaging, the operator adjusts the height position of the frame 18 or repositions the subject S. In a case in which the height position of the frame 18 and the positioning of the subject S are appropriate for imaging, the operator inputs an imaging instruction through the irradiation switch. The imaging instruction is received by the receiving unit 110 (YES in Step ST130). Therefore, imaging is performed in a first imaging mode (Step ST140).

For example, as illustrated in a table 120 of FIG. 15, in the first imaging mode, imaging is performed in the state illustrated in FIG. 11 in which the height position of the second imaging unit 302 is set to the lower end position and the imaging range is the first imaging range CR1 exceeding the width W of the detection surface 58 of one radiation detector 21. The rotation angle of the imaging unit 30 (frame 18) in the first imaging mode is 360°, and the rotation direction thereof is the clockwise direction CW. 360° is an example of a "first set angle" according to the technology of the present disclosure. In addition, the clockwise direction CW is an example of a "first direction" according to the technology of the present disclosure. In addition, strictly speaking, the rotation angle is 360°+θ.

The imaging time in the first imaging mode is 10 seconds. Since the rotation angle is 360°, the imaging unit 30 (frame 18) is rotated by 36° per second.

The frame rate of the radiation detector 21 in the first imaging mode is 30 frames per second (fps). Since the imaging time is 10 seconds, 300 projection images are output from one radiation detector 21 in the first imaging mode. Therefore, the radiation detector 21 outputs one projection image at every 1.2°. In this example, since the two imaging units 30 of the first imaging unit 301 and the second imaging unit 302 are provided, a total of 600 projection images are obtained.

In the first imaging mode, the rotation mechanism 45 is operated under the control of the imaging control unit 112 to rotate the frame 18 by 360° in the clockwise direction CW. Meanwhile, under the control of the imaging control unit 112, the radiation R is continuously emitted from the radiation source 20 under the same irradiation conditions with a period corresponding to the frame rate of the radiation detector 21, and the projection image is output from the radiation detector 21 whenever the radiation R is continuously emitted. Specifically, the first radiation source 201 and the second radiation source 202 emit the first radiation R1 and the second radiation R2 at the same time, and the first radiation detector 211 and the second radiation detector 212 output the projection images at the same time. Here, the period corresponding to the frame rate of the radiation detector 21 is the time (about 0.03 seconds) when the frame 18 is rotated by 1.2°. In addition, the "same time" means the same time including an error which is generally allowed in the technical field to which the technology of the present disclosure belongs and is not contrary to the gist of the technology of the present disclosure, in addition to the exact same time.

Figure 16:
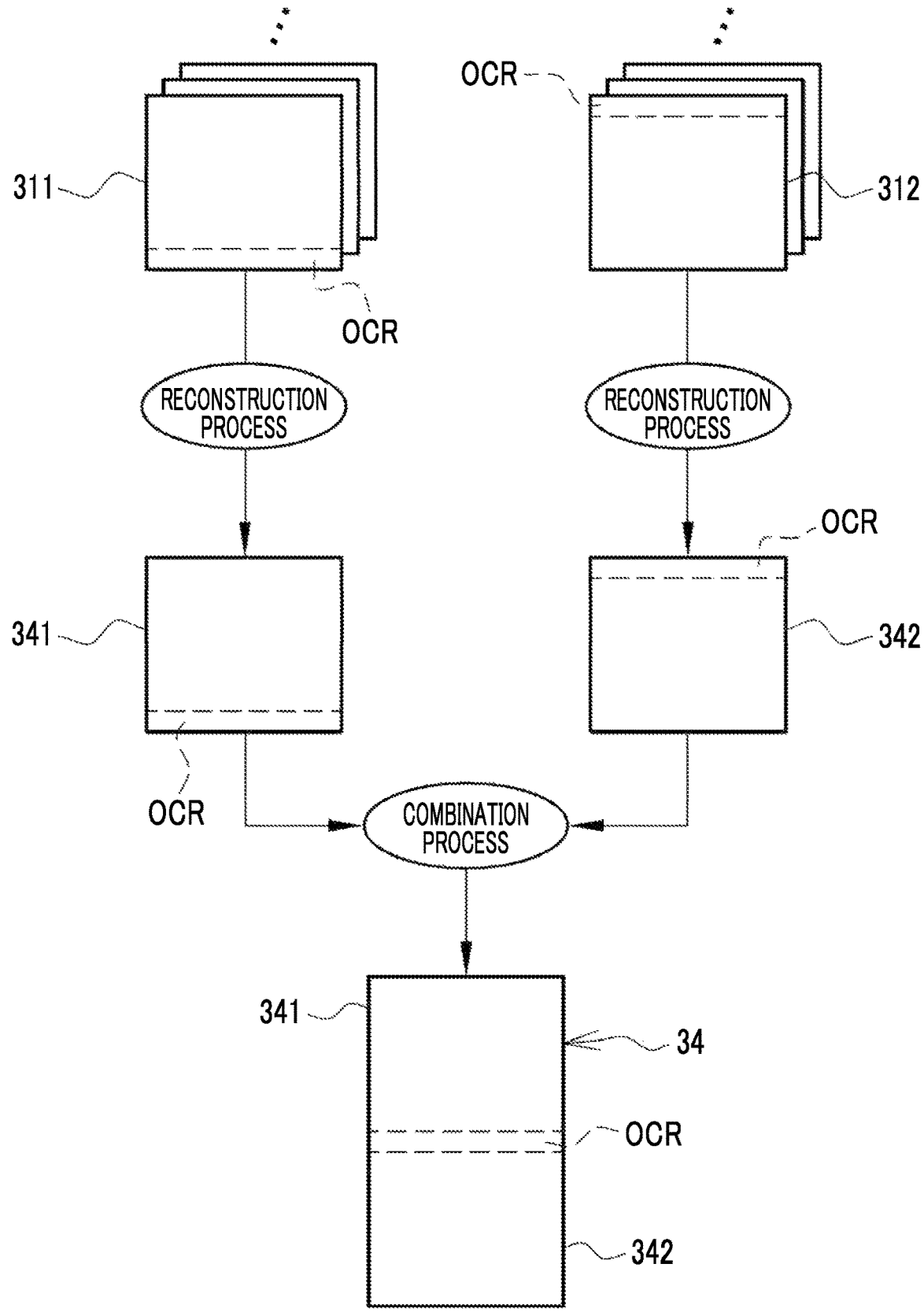
FIG. 16 is a diagram illustrating an outline of a process of generating a tomographic image from projection images.

Returning to FIG. 14, after the imaging in the first imaging mode ends, the image processing unit 113 generates a tomographic image for image analysis from the obtained projection images (Step ST150). Specifically, as illustrated in FIG. 16, a first tomographic image 341 and a second tomographic image 342 are generated from the first projection images 311 obtained by the first imaging unit 301 disposed at the upper end position and the second projection images 312 obtained by the second imaging unit 302 disposed at the lower end position, respectively. Then, the first tomographic image 341 and the second tomographic image 342 are registered on the basis of the overlapping imaging range OCR and are combined to generate a tomographic image 34 for image analysis. In this case, a process may be performed using a sigmoid function to smoothly connect the first tomographic image 341 and the second tomographic image 342 in the overlapping imaging range OCR. Then, the image analysis unit 114 specifies the suspected part in the tomographic image 34 for image analysis (Step ST150). Then, the height position information of the suspected part is output from the image analysis unit 114 to the imaging control unit 112.

After the imaging in the first imaging mode ends, the radiation source elevating mechanism 70 and the detector elevating mechanism 80 are operated under the control of the imaging control unit 112 to move the second radiation source 202 and the second radiation detector 212 (second imaging unit 302) to the upper end position (Step ST160). Further, in a case in which the height position information of the suspected part is input from the image analysis unit 114 to the imaging control unit 112, the frame elevating mechanism 35 is operated under the control of the imaging control unit 112 to move the frame 18 to the height position corresponding to the suspected part (Step ST170). Then, imaging is performed in a second imaging mode (Step ST180).

As illustrated in the table 120 of FIG. 15, in the second imaging mode, imaging is performed in the state illustrated in FIG. 12 in which the height position of the second imaging unit 302 is the upper end position and the imaging range is the second imaging range CR2 within the width W of the detection surface 58 of one radiation detector 21. The rotation angle of the imaging unit 30 (frame 18) in the second imaging mode is 240°. The rotation direction is the counterclockwise direction CCW that is opposite to the clockwise direction CW in the first imaging mode. 240° is an example of a "second set angle" according to the technology of the present disclosure. Further, the counterclockwise direction CCW is an example of a "second direction" according to the technology of the present disclosure. In addition, strictly speaking, the rotation angle is 240°+θ.

In the second imaging mode, the height positions of the first imaging unit 301 and the second imaging unit 302 are aligned with the same upper end position. Further, as illustrated in FIG. 8, the first radiation source 201 and the second radiation source 202 are disposed at positions that are separated by an angle of 120°. Therefore, in a case in which the frame 18 is rotated by 240°, an angular range of 360° is covered.

The imaging time in the second imaging mode is about 6.7 seconds that is shorter than 10 seconds in the first imaging mode since the rotation angle is 240°.

The frame rate of the radiation detector 21 in the second imaging mode is 30 fps which is the same as that in the first imaging mode. Since the imaging time is about 6.7 seconds, 200 projection images are output from one radiation detector 21 in the second imaging mode. In the second imaging mode, as in the first imaging mode, the radiation detector 21 outputs one projection image at every 1.2°. In this example, since the two imaging units 30 of the first imaging unit 301 and the second imaging unit 302 are provided, a total of 400 projection images are obtained.

In the second imaging mode, the rotation mechanism 45 is operated under the control of the imaging control unit 112 to rotate the frame 18 by 240° in the counterclockwise direction CCW from the rotation position at the end of the first imaging mode. Meanwhile, under the control of the imaging control unit 112, the radiation R is continuously emitted from the radiation source 20 with a period corresponding to the frame rate of the radiation detector 21, and the projection image is output from the radiation detector 21 whenever the radiation R is continuously emitted. In the second imaging mode, as in the first imaging mode, the first radiation source 201 and the second radiation source 202 emit the radiation R at the same time, and the first radiation detector 211 and the second radiation detector 212 output the projection images at the same time.

In the second imaging mode, the first imaging unit 301 is in charge of imaging in an angular range of 0° to 240°, and the second imaging unit 302 is in charge of imaging in an angular range of 120° to 360°. That is, the imaging of the entire circumference around the body axis of the subject S is shared by the first imaging unit 301 and the second imaging unit 302. The projection images obtained by the first imaging unit 301 and the second imaging unit 302 in the overlapping angular range, here, an angular range of 120° to 240° are discarded without being used for generating the tomographic images. In addition, the projection images obtained by the first imaging unit 301 and the second imaging unit 302 in the overlapping angular range may be used for checking the accuracy of the time when the projection images are captured.

Returning to FIG. 14, after the imaging in the second imaging mode ends, the image processing unit 113 generates a tomographic image for diagnosis from the obtained projection images (Step ST190). Then, under the control of the display control unit 115, the tomographic image for diagnosis is displayed on, for example, the display 98 and is provided for viewing by the operator (Step ST190).

As described above, the CT apparatus 10 comprises a plurality of imaging units 30, the rotation mechanism 45, the radiation source elevating mechanism 70, the detector elevating mechanism 80, and the CPU 97. The imaging unit 30 is composed of the radiation source 20 that emits the radiation R having a quadrangular pyramid shape to the subject S and the radiation detector 21 in which a plurality of pixels 57 detecting the radiation R transmitted through the subject S are two-dimensionally arranged. The rotation mechanism 45 rotates the plurality of imaging units 30 around the body axis of the subject S. The radiation source elevating mechanism 70 and the detector elevating mechanism 80 change the interval between the plurality of imaging units 30 in the rotation axis direction RAD. The imaging control unit 112 of the CPU 97 controls the operations of the plurality of imaging units 30, the rotation mechanism 45, the radiation source elevating mechanism 70, and the detector elevating mechanism 80. Therefore, it is possible to perform both the imaging of a relatively wide range and the imaging of a relatively narrow range in a short time.

In a case in which the imaging of the relatively wide range is performed by the CT apparatus described in JP2006-187453A, it is necessary to position the subject S in the gantry, to move the gantry several times in the body axis direction of the subject S, and to perform the imaging. Therefore, it takes a long time from the positioning of the subject S to the end of imaging, as compared to the CT apparatus 10 according to the technology of the present disclosure in which the subject S is guided into the apparatus main body 11 and then positioned after the second imaging unit 302 is moved to the lower end position. Therefore, the burden on the subject S increases. In addition, in a case in which the body movement of the subject S occurs at the time when the gantry is moved several times in the body axis direction of the subject S, the quality of the tomographic image deteriorates. On the other hand, in the CT apparatus 10 according to the technology of the present disclosure, it is possible to complete the imaging of a relatively wide range in a short time. Therefore, the burden on the subject S is reduced, and the concern that the quality of the tomographic image will deteriorate due to the body movement of the subject S is also reduced.

As illustrated in FIG. 7, the radiation source 20 emits the radiation R having a quadrangular pyramid shape, and the radiation detector 21 has the configuration in which the plurality of pixels 57 detecting the radiation R are two-dimensionally arranged. Therefore, it is possible to complete imaging in a short time, as compared to the CT apparatus according to the related art in which a radiation source emits the radiation R having a fan shape and a radiation detector in which pixels are one-dimensionally arranged detects the radiation R. In addition, the radiation R having a conical shape instead of the quadrangular pyramid shape may be emitted.

The imaging control unit 112 controls switching between the first imaging mode in which imaging is performed with a relatively large interval between the plurality of imaging units 30 in the rotation axis direction RAD and the second imaging mode in which imaging is performed with a relatively small interval therebetween. Therefore, it is possible to smoothly perform the imaging in which the interval between the plurality of imaging units 30 in the rotation axis direction RAD is relatively large and the imaging in which the interval is relatively small with one CT apparatus 10. The burden on the subject S is reduced as compared to a case in which the imaging in which the interval is relatively large and the imaging in which the interval is relatively small are performed by different apparatuses. In addition, it is possible to secure the reproducibility of the positioning of the subject S in the imaging in which the interval is relatively large and the imaging in which the interval is relatively small.

As illustrated in FIGS. 11 and 15, the first imaging mode is a mode in which the first imaging range CR1 that exceeds the width W of the detection surface 58 for the radiation R in the radiation detector 21 is imaged. The rotation angle of the plurality of imaging units 30 around the body axis in the first imaging mode is the first set angle that is equal to or greater than 180°. Therefore, in the first imaging mode, it is possible to obtain the tomographic image, which covers the first imaging range CR1 exceeding the width W of the detection surface 58 for the radiation R in the radiation detector 21, in a short time.

As illustrated in FIG. 11, the imaging control unit 112 sets the interval between the imaging units 30 in the rotation axis direction RAD such that the overlapping imaging range OCR occurs between the projection images obtained by adjacent imaging units 30. As illustrated in FIG. 16, the image processing unit 113 performs the reconstruction process on the projection images (the first projection images 311 and the second projection images 312) obtained from each of the plurality of imaging units 30 to generate a plurality of tomographic images (the first tomographic image 341 and the second tomographic image 342) for each of the plurality of imaging units 30. The image processing unit 113 registers the plurality of tomographic images on the basis of the overlapping imaging range OCR to combine the plurality of tomographic images. Therefore, it is possible to capture the tomographic image covering the first imaging range CR1 that exceeds the width W of the detection surface 58 for the radiation R in the radiation detector 21. In addition, after the projection images obtained from each of the imaging units 30 are registered on the basis of the overlapping imaging range OCR and combined, the reconstruction process may be performed on the combined projection images to generate the tomographic images.

As illustrated in FIGS. 12 and 15, the second imaging mode is a mode in which the second imaging range CR2 within the width W of the detection surface 58 for the radiation R in the radiation detector 21 is imaged. The rotation angle of the plurality of imaging units 30 around the body axis in the second imaging mode is the second set angle corresponding to the phases of the first imaging unit 301 and the second imaging unit 302 in the rotation direction. The plurality of imaging units 30 are rotated at the second set angle such that the imaging of the entire circumference around the body axis is shared by the plurality of imaging units 30. Therefore, it is possible to obtain the tomographic image, which covers the second imaging range CR2 within the width W of the detection surface 58 for the radiation R in the radiation detector 21, in a short time.

As illustrated in FIG. 15, in a case in which the first imaging mode and the second imaging mode are continuously performed, the imaging control unit 112 rotates the plurality of imaging units 30 in the clockwise direction CW in the first imaging mode and rotates the plurality of imaging units 30 in the counterclockwise direction CCW in the second imaging mode. Therefore, it is not necessary to provide a special mechanism, such as a slip ring, that allows a rotation of 360° or more, and it is possible to simplify the configuration of the apparatus.

Figure 17:
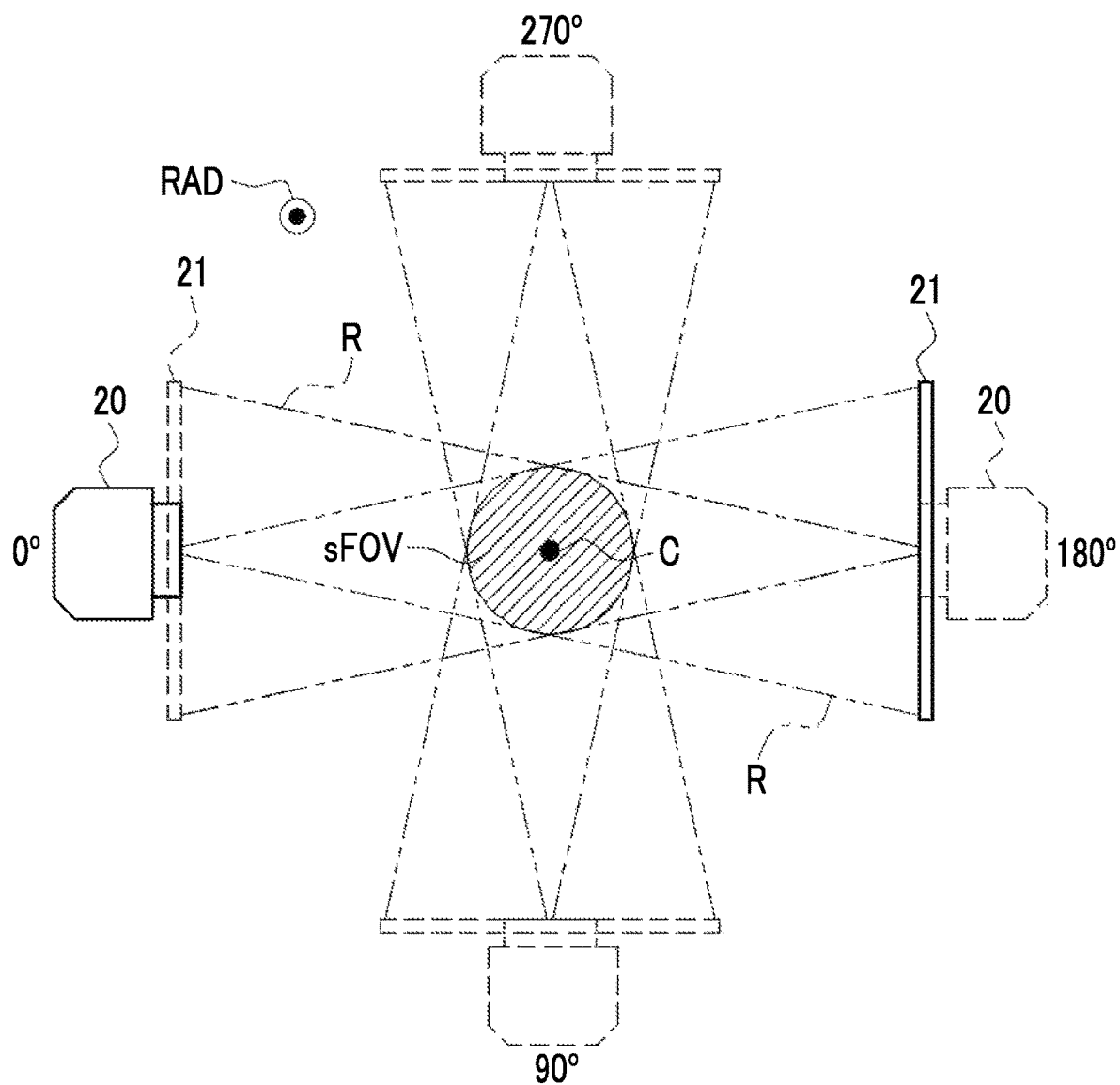
FIG. 17 is a diagram illustrating a scan field of view in a case in which the radiation detector is located at the reference position.
Figure 18:
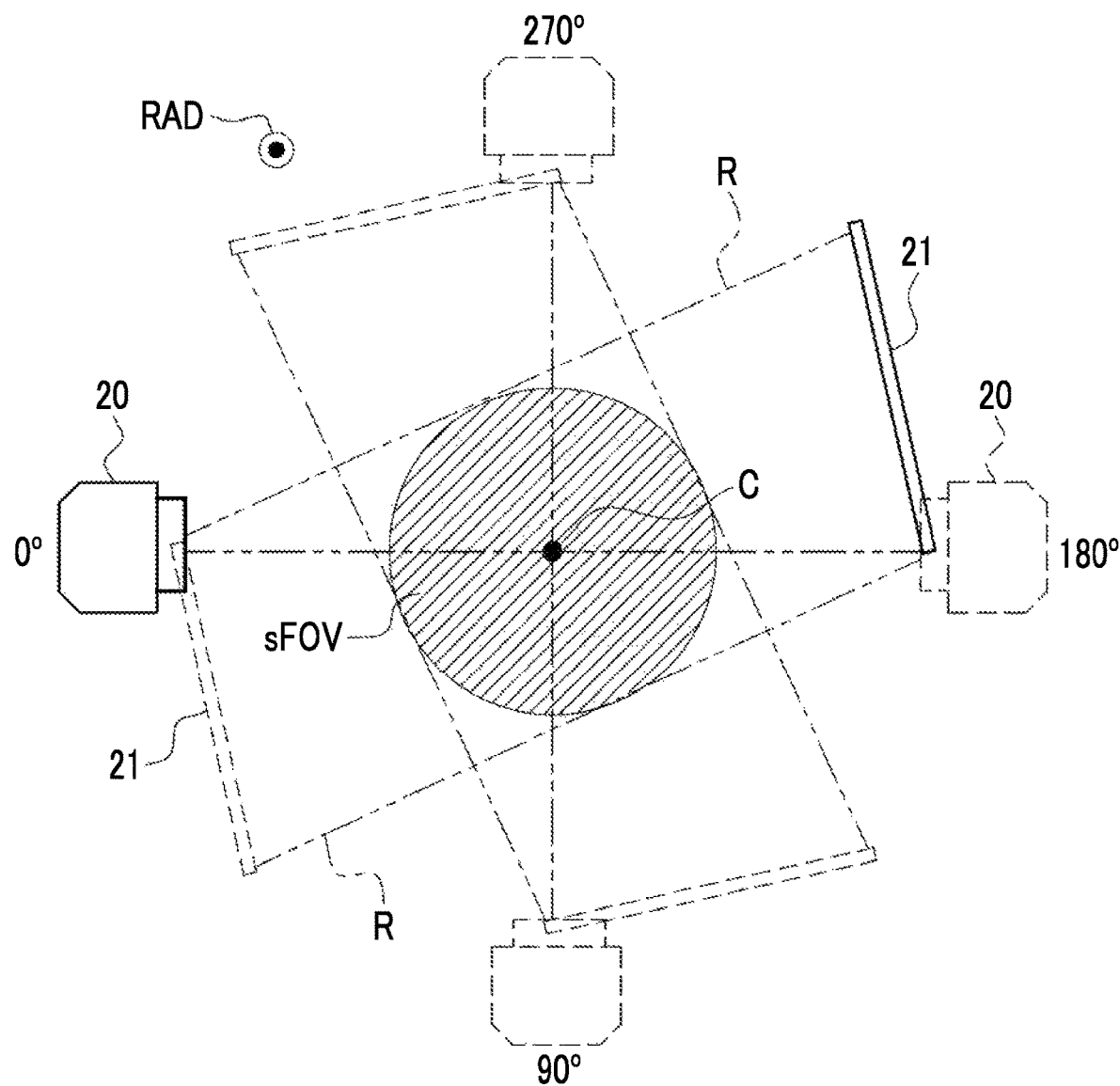
FIG. 18 is a diagram illustrating a scan field of view in a case in which the radiation detector is located at the offset position.

Here, as illustrated in FIG. 17, in a case in which the radiation detector 21 is disposed at the reference position, the region to be scanned does not change with a rotation of 360°. Therefore, a scan field of view sFOV stays in a relatively small region as represented by hatching. On the other hand, as illustrated in FIG. 18, in a case in which the radiation detector 21 is disposed at the offset position, the region to be scanned changes with a rotation of 360°. Therefore, the scan field of view sFOV is a relatively large region as represented by hatching. Therefore, as illustrated in FIG. 9, in a case in which the radiation detector 21 is disposed at the offset position that is separated from the reference position facing the radiation source 20 by a preset angle as viewed from the rotation axis direction RAD, it is possible to widen the scan field of view sFOV, as compared to a case in which the radiation detector 21 is disposed at the reference position. In addition, the angle φ can be set to be slightly larger than that in a case in which the radiation detector 21 is disposed at the reference position. In addition, the first set angle in a case in which the radiation detector 21 is disposed at the reference position as illustrated in FIG. 17 is 180° (strictly speaking, 180°+θ).

The plurality of imaging units 30 are held by the frame 18, and the subject S is positioned in the frame 18. As illustrated in FIG. 8, as viewed from the rotation axis direction RAD, the radiation source 20 is disposed outside the frame 18, and the radiation detector 21 is disposed inside the frame 18. The scan field of view sFOV increases as the radiation source 20 is further away from the subject S and as the radiation detector 21 is closer to the subject S. Therefore, in a case in which the radiation source 20 is disposed outside the frame 18 in which the subject S is positioned and the radiation detector 21 is disposed inside the frame 18, it is possible to widen the scan field of view sFOV.

As illustrated in FIG. 3, the plurality of imaging units 30 are two imaging units of the first imaging unit 301 and the second imaging unit 302. As illustrated in FIG. 8, in a case in which the position where the first radiation source 201 of the first imaging unit 301 is disposed is 0° as viewed from the rotation axis direction RAD, the second radiation source 202 of the second imaging unit 302 is disposed at a position that is separated from the first radiation source 201 by an angle φ that is equal to or greater than 90° and equal to or less than 120°.

In a case in which the angle φ is less than 90°, the rotation angle in the second imaging mode approaches 360° in the first imaging mode, and the imaging time is almost the same as that in the first imaging mode. Therefore, the effect of shortening the imaging time by providing the first imaging unit 301 and the second imaging unit 302 is small. In addition, in a case in which the angle φ is greater than 120°, the end of the second radiation detector 212 is included in the projection image obtained by the first imaging unit 301, as in the case illustrated in FIG. 19 in which the angle φ is 125°. Therefore, it is preferable that the angle φ is equal to or greater than 90° and equal to or less than 120°.

Figure 19:
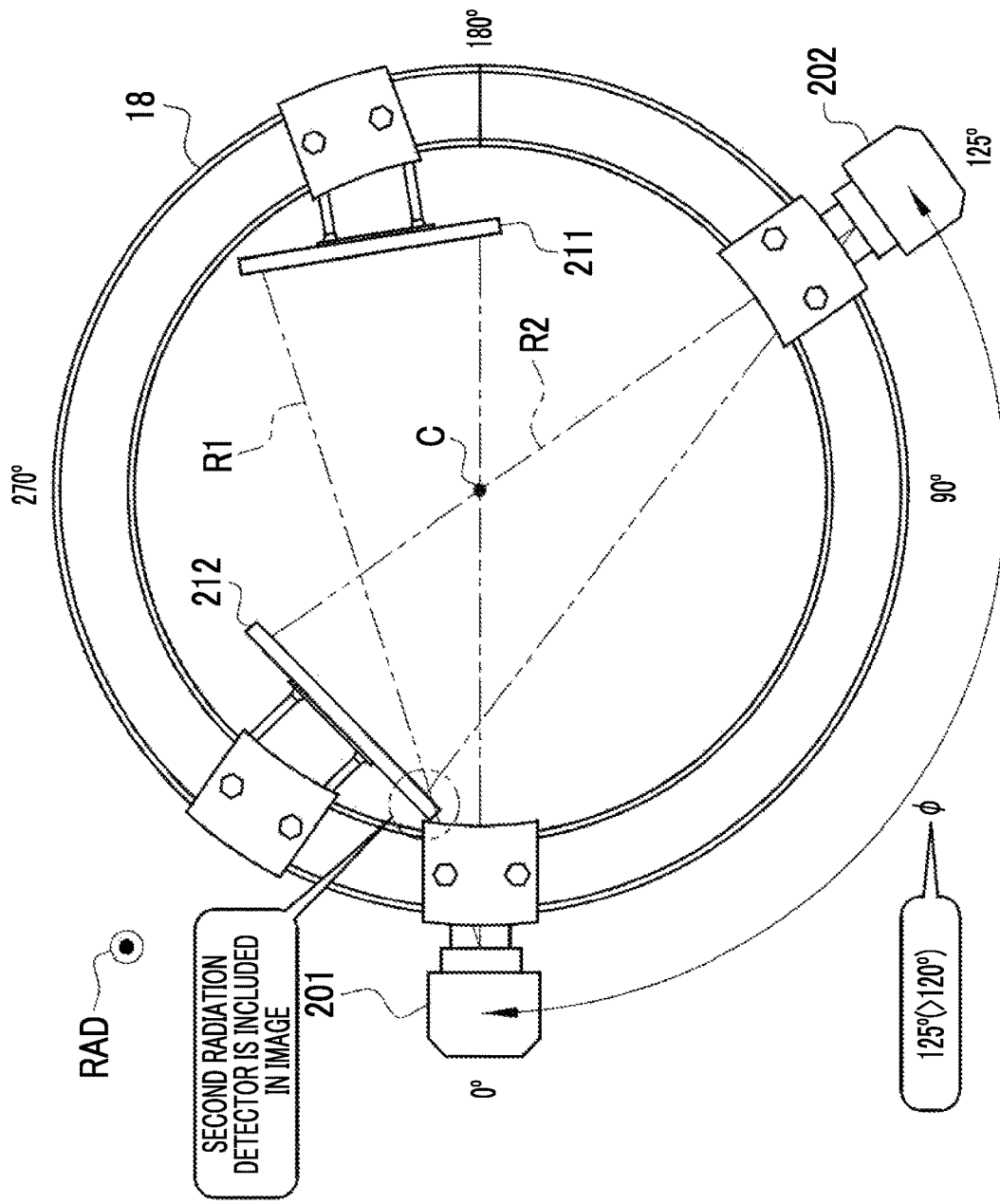
FIG. 19 is a diagram illustrating a case in which a second radiation source is disposed at a position separated from a first radiation source by an angle greater than 120°.

In addition, in a case in which the size of the radiation detector 21 is reduced, it is avoided that the radiation detector 21 is included in the projection image as illustrated in FIG. 19 even though the angle φ is greater than 120°. However, as the size of the radiation detector 21 is reduced, the scan field of view sFOV is narrowed. Further, in a case in which the rotation radius of the radiation detector 21 (the distance between the rotation center C and the center point CS of the detection surface 58 of the radiation detector 21) increases, the angle φ can be greater than 120°. However, since the radiation detector 21 is separated from the subject S, the scan field of view sFOV is also reduced in this case. Therefore, it is preferable that the ratio of the rotation radius of the radiation source 20 (the distance between the rotation center C and the focus of the radiation R of the radiation source 20) to the rotation radius of the radiation detector 21 is set to about 2:1 (for example, the rotation radius of the radiation source 20 is 800 mm, and the rotation radius of the radiation detector 21 is 400 mm)) to secure a relatively wide scan field of view sFOV.

Alternatively, in a case in which the size of the frame 18 increases to increase the SID, the angle φ can be greater than 120° without separating the radiation detector 21 from the subject S. However, it is necessary to prepare a high-output rotary motor 47 in accordance with the frame 18 that has become larger and heavier, or it is necessary to thicken the columns 14 to increase rigidity. In addition, it is necessary to increase the power of the radiation R as the SID is longer. From the above, it is also preferable that the angle φ is equal to or greater than 90° and equal to or less than 120°.

As illustrated in FIGS. 1, 2, and 4, the subject S is positioned in either the standing posture or the sitting posture. Therefore, it is possible to meet the demand to observe soft tissues, such as the lungs, in a natural state in which gravity is applied or to observe joints, such as hip joints, in a state in which gravity is applied and a load is applied. In addition, the CT apparatus may be used to image the subject S in a decubitus posture.

Figure 20:
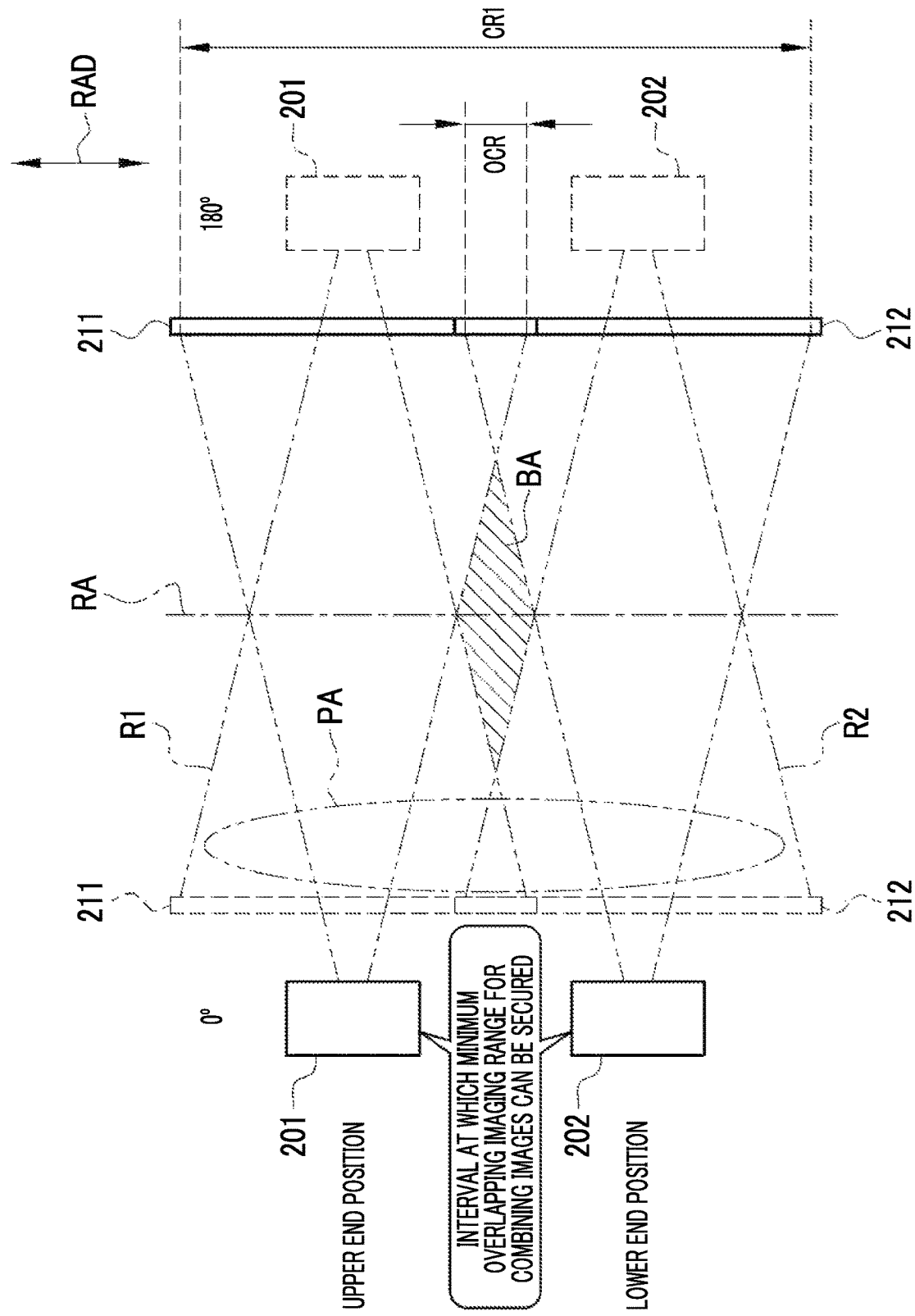
FIG. 20 is a diagram illustrating another example of the positions of the first imaging unit and the second imaging unit in the first imaging mode.

In the example illustrated in FIG. 11, the lower end position is set as a position where the lower end RILE of the flux of the first radiation R1 is matched with the upper end R2UE of the flux of the second radiation R2. However, the present disclosure is not limited thereto. For example, as illustrated in FIG. 20, the lower end position may be lower than that in the case illustrated in FIG. 11 as long as the interval has a value at which the minimum overlapping imaging range OCR for combining the tomographic image generated from the projection images obtained by the first imaging unit 301 with the tomographic image generated from the projection images obtained by the second imaging unit 302 can be secured. This makes it possible to further widen the first imaging range CR1. However, in this case, as represented by hatching, a blank region BA that is not irradiated with either the first radiation R1 or the second radiation R2 occurs in the vicinity of the rotation center C. Therefore, the subject S is positioned in a region PA avoiding the blank region BA. It is possible to image a relatively wide range even though the quality of the tomographic image deteriorates to some extent. In addition, the minimum overlapping imaging range OCR is, for example, 10 mm to 30 mm.

Figure 21:
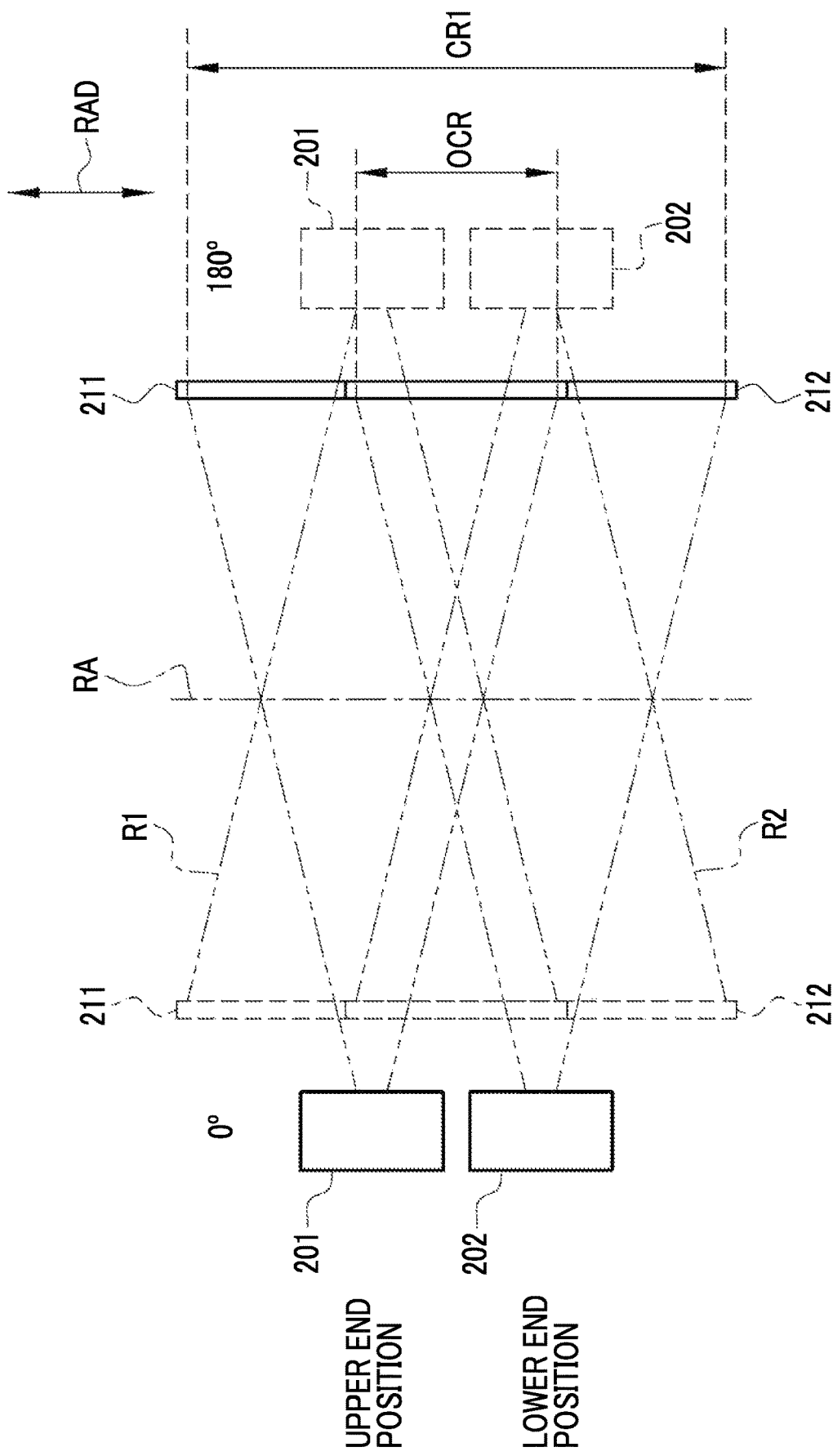
FIG. 21 is a diagram illustrating still another example of the positions of the first imaging unit and the second imaging unit in the first imaging mode.

Further, for example, as illustrated in FIG. 21, the lower end position may be a position where the flux of the second radiation R2 partially overlaps the flux of the first radiation R1.

Figure 22:
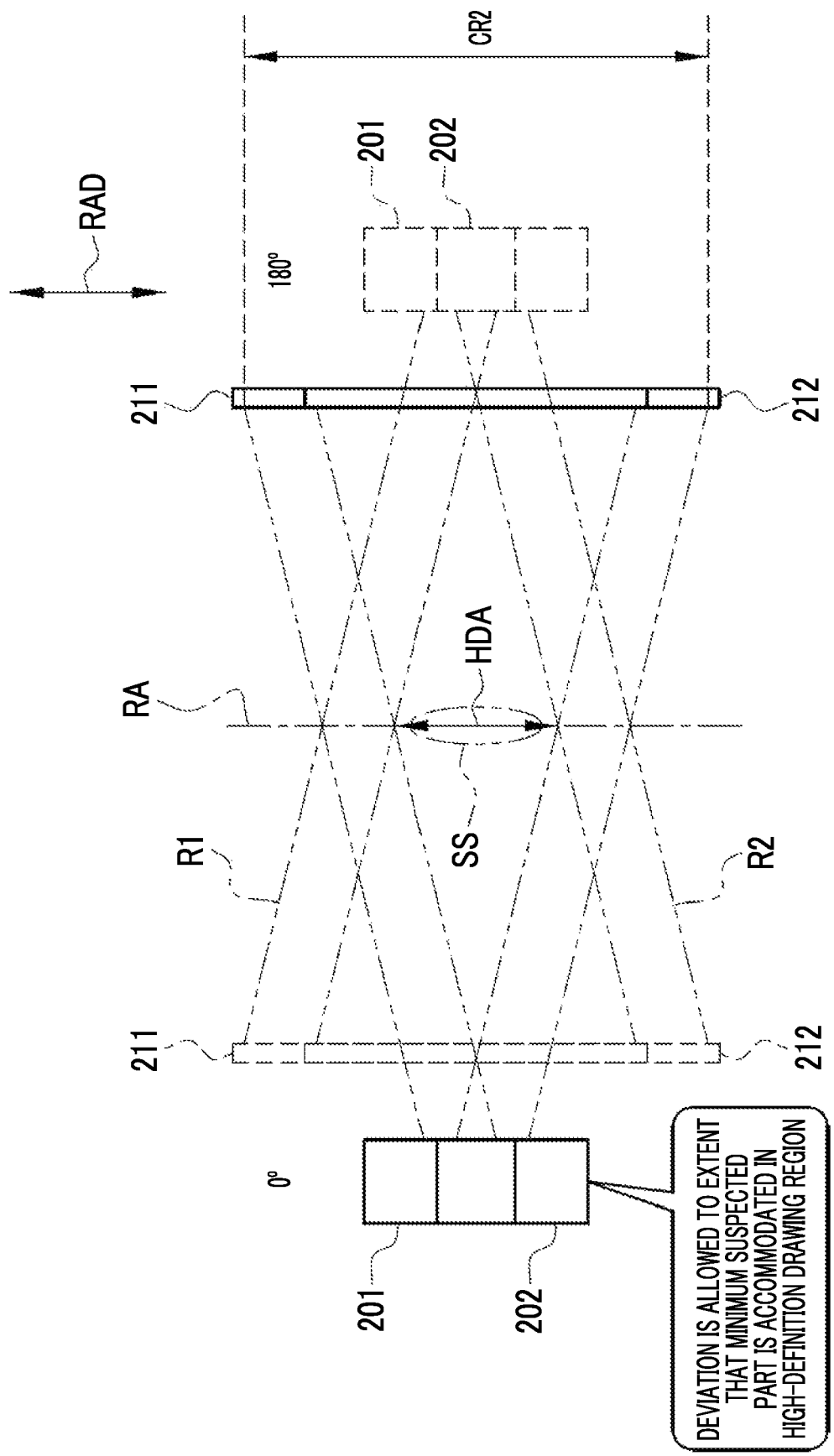
FIG. 22 is a diagram illustrating yet another example of the positions of the first imaging unit and the second imaging unit in the second imaging mode.

In the second imaging mode, as illustrated in FIG. 12, the flux of the first radiation R1 and the flux of the second radiation R2 are matched with each other. However, the present disclosure is not limited thereto. For example, as illustrated in FIG. 22, a deviation may be allowed to the extent that a minimum suspected part SS is accommodated in the high-definition drawing region HDA between the flux of the first radiation R1 and the flux of the second radiation R2 (the width of the high-definition drawing region HDA in the rotation axis direction RAD≥the width of the minimum suspected part SS in the rotation axis direction RAD). In this case, the second imaging range CR2 actually slightly exceeds the width W of the detection surface 58 of the radiation detector 21. However, it is assumed that the second imaging range CR2 is within the width W. The high-definition drawing region HDA is smaller as the interval between the first imaging unit 301 and the second imaging unit 302 is larger. In a case in which the width of the high-definition drawing region HDA in the rotation axis direction RAD is smaller than the width of the minimum suspected part SS in the rotation axis direction RAD, the high-definition drawing region HDA is the upper limit of the allowable amount of deviation between the flux of the first radiation R1 and the flux of the second radiation R2. The minimum suspected part SS is, for example, one vertebra of a child and is about 15 mm.

Second Embodiment

For example, as illustrated in a table 125 of FIG. 23, a plurality of sub-imaging modes may be provided in the first imaging mode. Specifically, there are three sub-imaging modes of a sub-imaging mode A, a sub-imaging mode B, and a sub-imaging mode C.

The sub-imaging mode A is a mode in which the interval has a value at which the lower end RILE of the flux of the first radiation R1 and the upper end R2UE of the flux of the second radiation R2 are matched with each other, as illustrated in FIG. 11. The sub-imaging mode A is applied to standard imaging such as whole spine imaging.

The sub-imaging mode B is a mode in which the interval has a value at which the minimum overlapping imaging range OCR for combining the tomographic image generated from the projection images obtained by the first imaging unit 301 with the tomographic image generated from the projection images obtained by the second imaging unit 302 can be secured as illustrated in FIG. 20. The sub-imaging mode B is applied to the imaging of a relatively wide imaging range such as a patient with scoliosis.

The sub-imaging mode C is a mode in which the interval has a value at which the flux of the second radiation R2 partially overlaps the flux of the first radiation R1 as illustrated in FIG. 21. The sub-imaging mode C is applied to the imaging of a relatively narrow imaging range such as a child.

As described above, in the second embodiment, the first imaging mode has a plurality of sub-imaging modes having different intervals. Therefore, it is possible to perform imaging in the first imaging mode at an interval adapted to the content of imaging.

Third Embodiment

Figure 24:
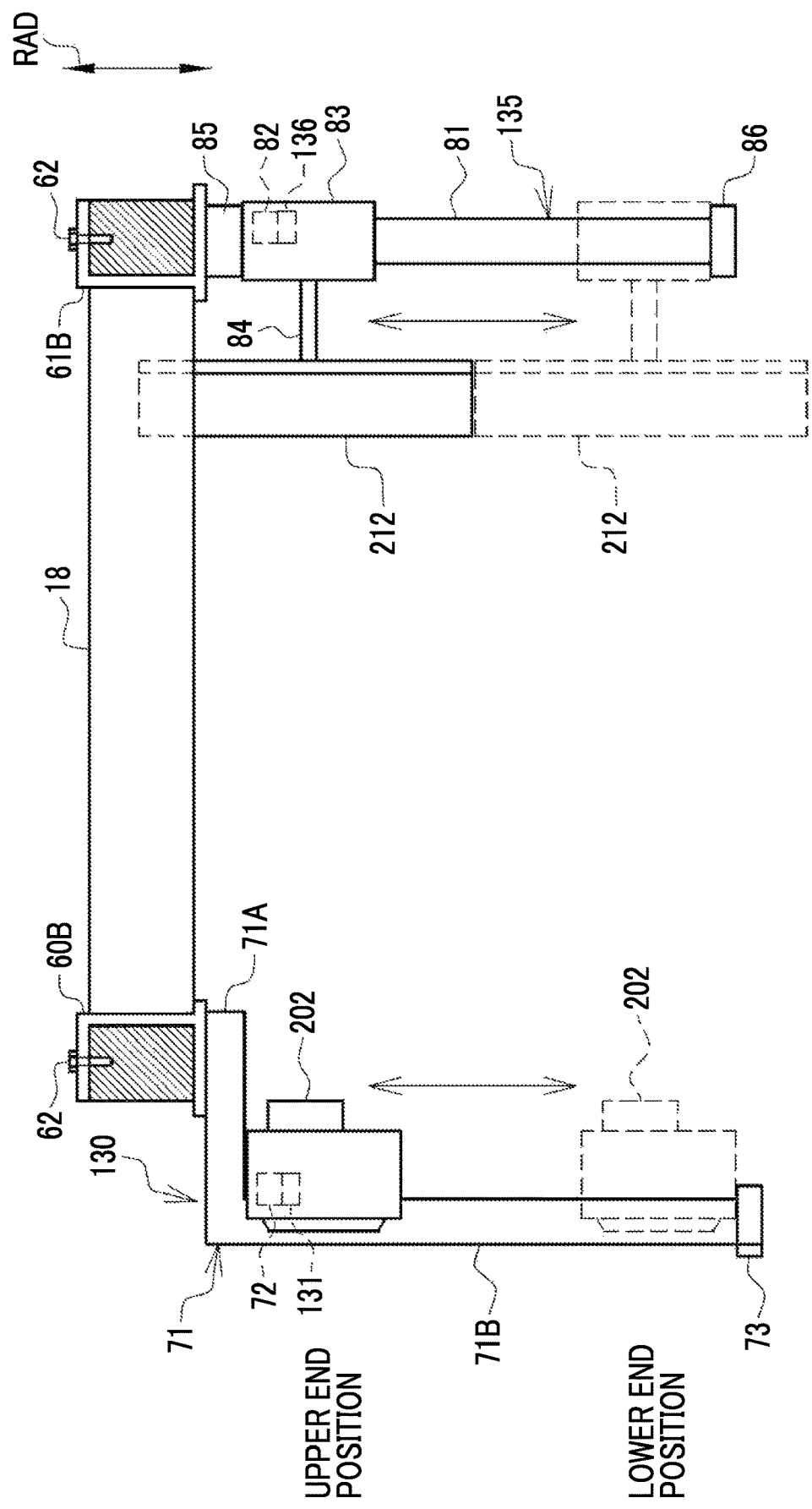
FIG. 24 is a diagram illustrating a radiation source elevating mechanism having a radiation source clutch and a detector elevating mechanism having a detector clutch.

For example, a radiation source elevating mechanism 130 and a detector elevating mechanism 135 illustrated in FIG. 24 may be used. The radiation source elevating mechanism 130 is configured by adding a radiation source clutch 131 to the guide rail 71, the radiation source elevating motor 72, and the like. The radiation source clutch 131 switches between the transmission and blocking of the driving force of the radiation source elevating motor 72 with respect to the second radiation source 202. The detector elevating mechanism 135 is configured by adding a detector clutch 136 to the guide rail 81, the detector elevating motor 82, and the like. The detector clutch 136 switches between the transmission and blocking of the driving force of the detector elevating motor 82 with respect to the elevating box 83 and thus the second radiation detector 212.

Figure 25:
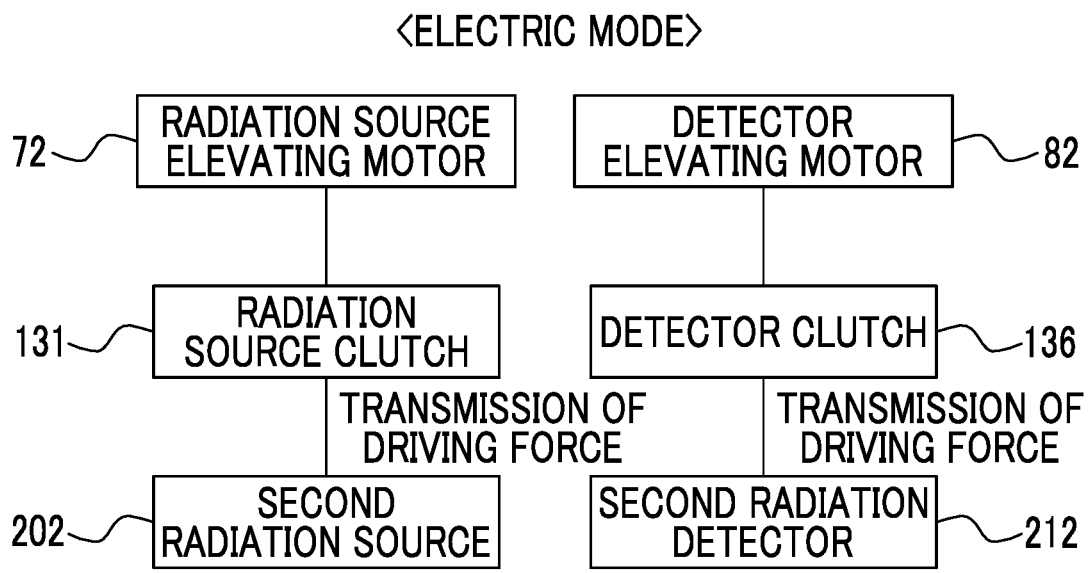
FIG. 25 is a diagram illustrating an electric mode.
Figure 26:
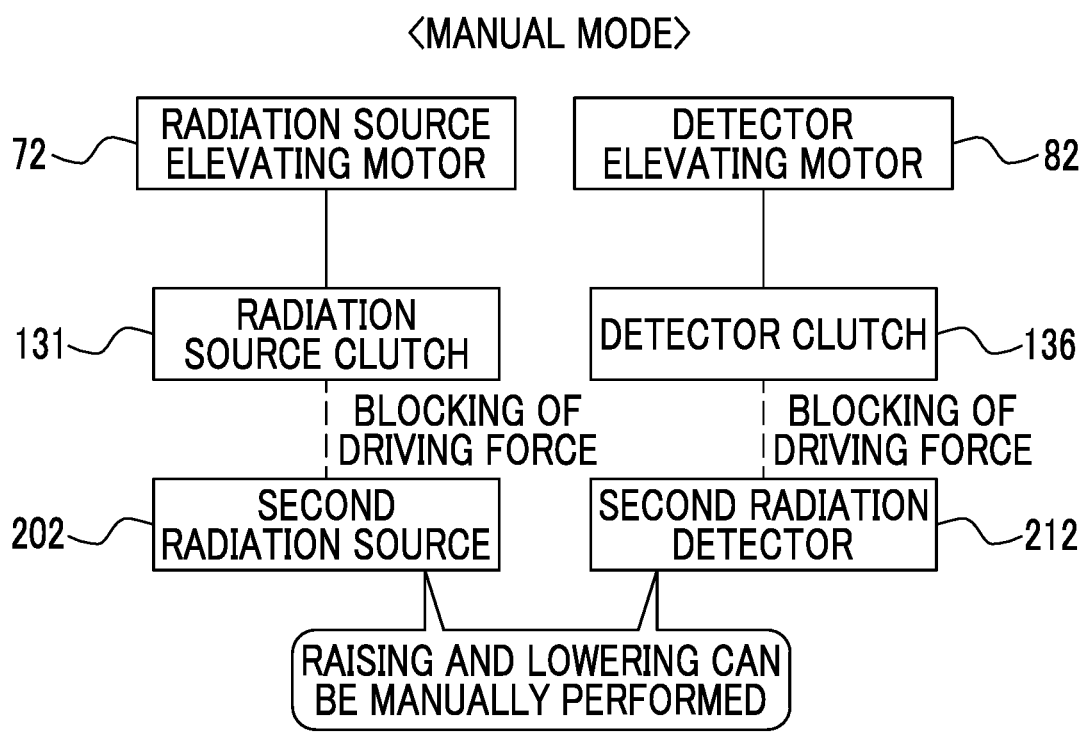
FIG. 26 is a diagram illustrating a manual mode.

For example, as illustrated in FIGS. 25 and 26, the radiation source elevating mechanism 130 and the detector elevating mechanism 135 have an electric mode and a manual mode. As illustrated in FIG. 25, in the electric mode, the driving force of the radiation source elevating motor 72 is transmitted to the second radiation source 202 by the radiation source clutch 131, and the second radiation source 202 is electrically raised and lowered. In addition, the driving force of the detector elevating motor 82 is transmitted to the elevating box 83 and thus the second radiation detector 212 by the detector clutch 136, and the second radiation detector 212 is electrically raised and lowered.

On the other hand, as illustrated in FIG. 26, in the manual mode, the transmission of the driving force of the radiation source elevating motor 72 is blocked by the radiation source clutch 131, which makes it possible to manually raise and lower the second radiation source 202. In addition, the transmission of the driving force of the detector elevating motor 82 is blocked by the detector clutch 136, which makes it possible to manually raise and lower the second radiation detector 212.

As described above, in the third embodiment, the radiation source elevating mechanism 130 and the detector elevating mechanism 135 have the electric mode in which the second imaging unit 302 is moved by the radiation source elevating motor 72 and the detector elevating motor 82 and the manual mode in which the second imaging unit 302 is manually moved. Therefore, it is possible to manually adjust the position of the second imaging unit 302.

Figure 27:
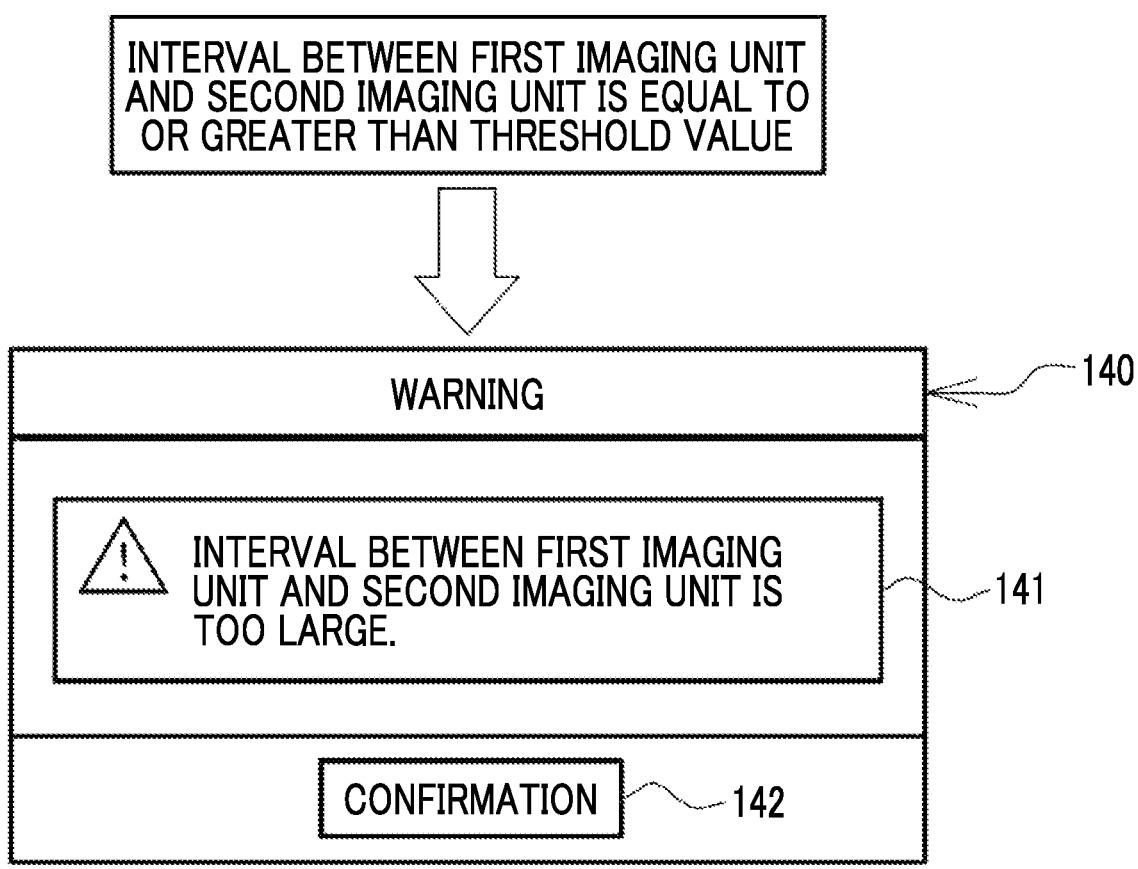
FIG. 27 is a diagram illustrating a warning screen that is displayed on a display in a case in which the interval between the first imaging unit and the second imaging unit is equal to or greater than a threshold value.

Further, in the manual mode, for example, in a case in which imaging in the first imaging mode is started and the interval between the first imaging unit 301 and the second imaging unit 302 is equal to or greater than a threshold value, a warning screen 140 illustrated in FIG. 27 as an example may be displayed on the display 98 under the control of the display control unit 115.

The warning screen 140 includes a message 141 indicating that the interval between the first imaging unit 301 and the second imaging unit 302 is too large. A confirmation button 142 is selected to remove the display of the warning screen 140. The interval at which the minimum overlapping imaging range OCR for combining the tomographic image generated from the projection images obtained by the first imaging unit 301 with the tomographic image generated from the projection images obtained by the second imaging unit 302 can be secured is set as the threshold value.

As described above, in the manual mode, in a case in which control is performed to warn that the interval between the first imaging unit 301 and the second imaging unit 302 is equal to or greater than the threshold value, it is possible to avoid a situation in which imaging is performed in a state in which the interval between the first imaging unit 301 and the second imaging unit 302 is inappropriate.

An interval at which the width of the high-definition drawing region HDA in the rotation axis direction RAD is smaller than the width of the minimum suspected part SS in the rotation axis direction RAD may be set as the threshold value. Then, in a case in which imaging in the second imaging mode is started and the interval between the first imaging unit 301 and the second imaging unit 302 is equal to or greater than the threshold value, the warning screen 140 may be displayed on the display 98. In addition, instead of or in addition to the warning screen 140, a warning may be issued by a lamp, voice, or the like.

Fourth Embodiment

Figure 28:
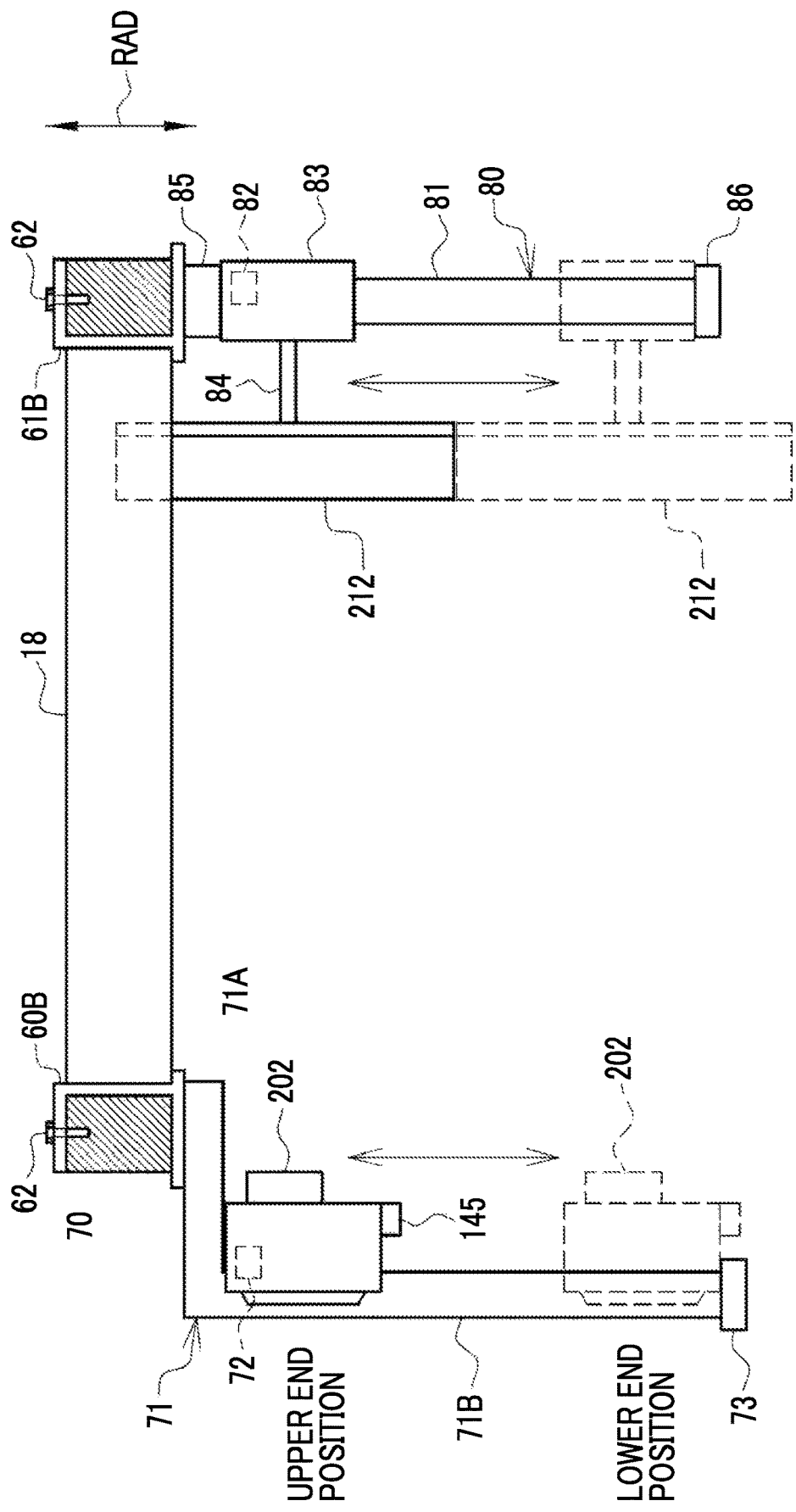
FIG. 28 is a diagram illustrating a third embodiment in which a camera is provided in the second radiation source.

For example, as illustrated in FIG. 28, a camera 145 may be provided in the second radiation source 202. The camera 145 images the subject S positioned in the apparatus main body 11. The camera 145 is raised or lowered in operative association with the second radiation source 202. The camera 145 is provided separately from the second radiation source 202 and is attached to a lower portion of the second radiation source 202 which does not interfere with the second radiation R2. In addition, the camera 145 may be integrated with the second radiation source 202 or may be provided in the second radiation source 202.

Figure 29:
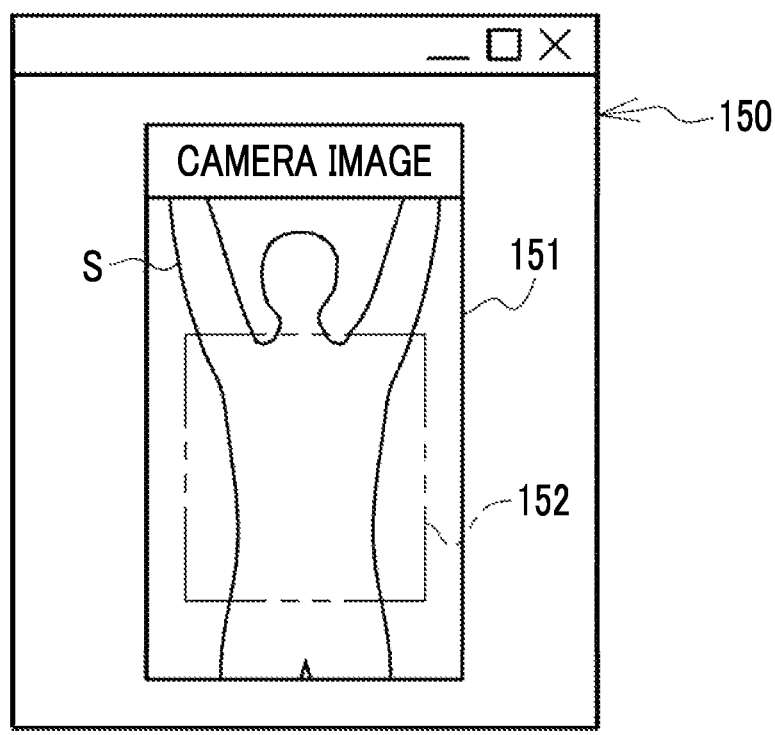
FIG. 29 is a diagram illustrating a camera image display screen.

For example, as illustrated in FIG. 29, the display control unit 115 performs control to display a camera image display screen 150 on the display 98. A camera image 151 obtained from the camera 145 is displayed on the camera image display screen 150. The subject S is included in the camera image 151. The display control unit 115 displays a frame 152 indicating an imaging range that can be reconstructed as a tomographic image to be superimposed on the camera image 151. The reconstructible imaging range may be a range corresponding to the scan field of view sFOV or may be a range corresponding to the high-definition drawing region HDA. The reconstructible imaging range can be derived from, for example, the SID, the size of the irradiation field, and the interval between the first imaging unit 301 and the second imaging unit 302.

As described above, in the fourth embodiment, the camera 145 that is moved in operative association with the second radiation source 202 is provided. The display control unit 115 performs control to display the camera image 151 obtained from the camera 145 on the display 98. Therefore, the operator can check, for example, the positional relationship between the second radiation source 202 and the subject S and the positioning aspect of the subject S through the camera image 151.

In addition, the display control unit 115 displays the frame 152 indicating the imaging range that can be reconstructed as the tomographic image to be superimposed on the camera image 151. Therefore, it is possible to inform the operator of the reconstructible imaging range. The operator can reposition the subject S with reference to the frame 152 or finely adjust the interval between the first imaging unit 301 and the second imaging unit 302.

The camera 145 may be provided in the second radiation detector 212 instead of the second radiation source 202. Further, the camera 145 may be disposed at a position different from the positions of the second radiation source 202 and the second radiation detector 212, for example, at a position of 90° illustrated in FIG. 8 and the like, and an elevating mechanism that raises and lowers the camera 145 in operative association with the second imaging unit 302 may be provided.

Fifth Embodiment

Figure 30:
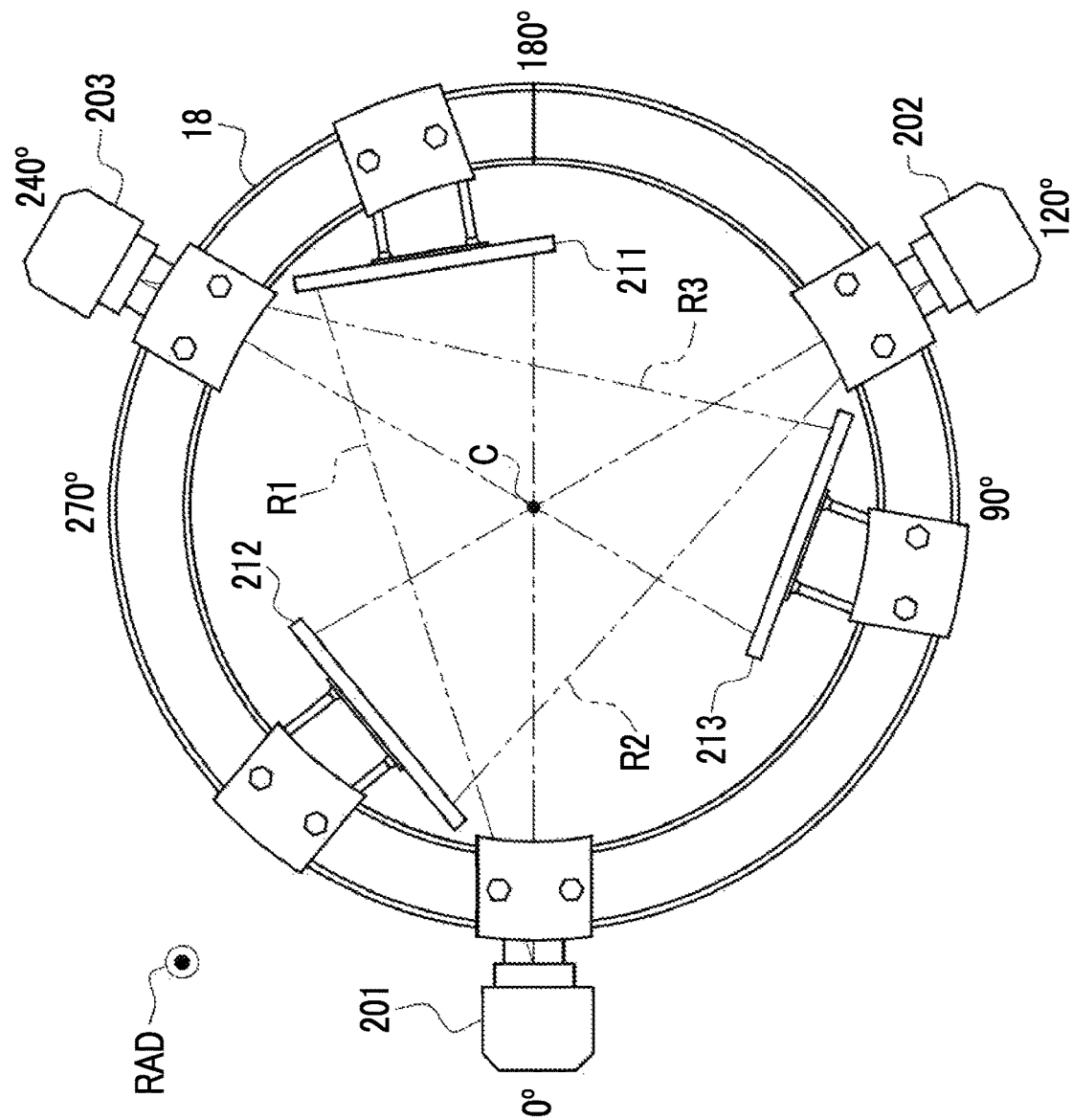
FIG. 30 is a diagram illustrating an example in which three imaging units are provided.
Figure 31:
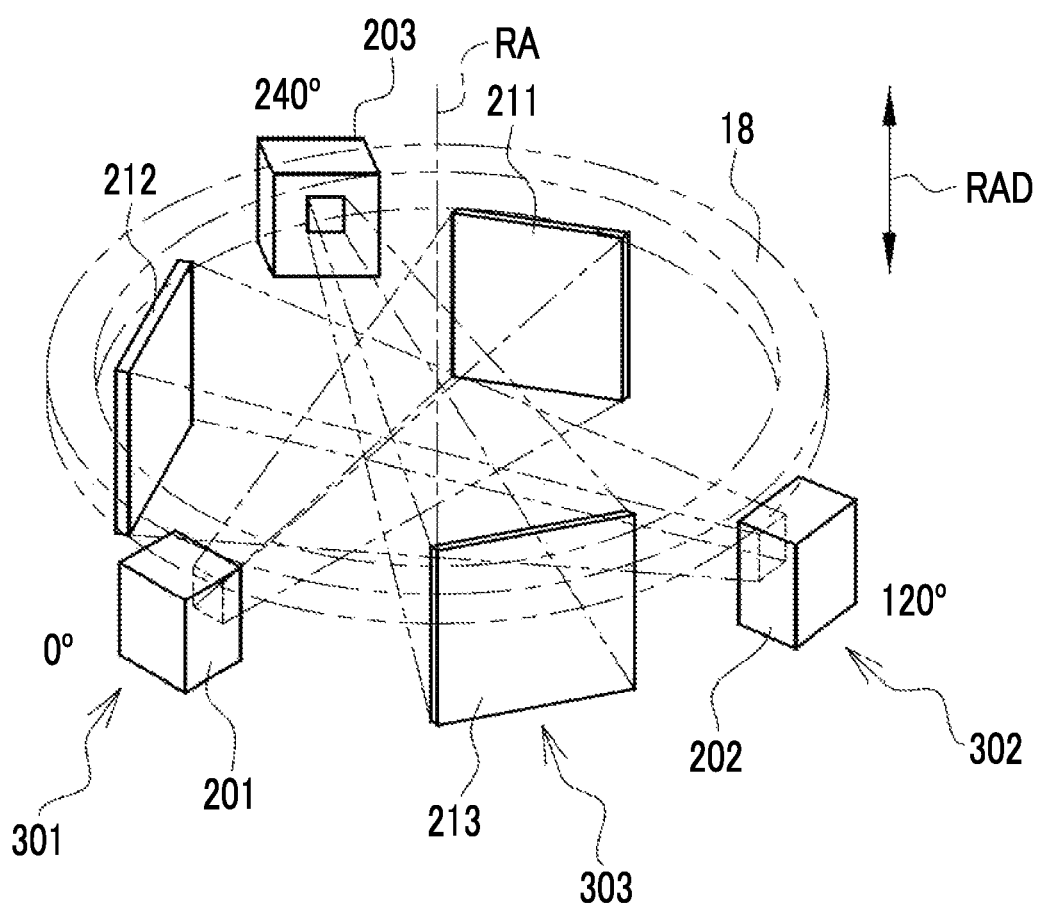
FIG. 31 is a diagram illustrating configurations of the first imaging unit, the second imaging unit, and a third imaging unit.

In each of the above-described embodiments, two imaging units 30 of the first imaging unit 301 and the second imaging unit 302 are given as an example. However, the number of imaging units 30 is not limited thereto. For example, as illustrated in FIGS. 30 and 31, three imaging units 30 of the first imaging unit 301, the second imaging unit 302, and a third imaging unit 303 may be provided.

The third imaging unit 303 is composed of a third radiation source 203 and a third radiation detector 213. The third radiation source 203 is disposed at a position that is separated from the first radiation source 201 by 240° and from the second radiation source 202 by 120° as viewed from the rotation axis direction RAD. The third radiation detector 213 is disposed at a position corresponding to the position where the third radiation source 203 is disposed. That is, the first imaging unit 301, the second imaging unit 302, and the third imaging unit 303 are disposed at every 120°.

In addition, all of the first radiation detector 211, the second radiation detector 212, and the third radiation detector 213 are disposed at the offset positions illustrated in FIG. 9. Further, the radiation source elevating mechanism and the detector elevating mechanism are provided in the second imaging unit 302 and the third imaging unit 303, and the second imaging unit 302 and the third imaging unit 303 are raised and lowered in the rotation axis direction RAD. On the other hand, the first imaging unit 301 is not provided with the radiation source elevating mechanism and the detector elevating mechanism as in the first embodiment. The first imaging unit 301 is fixed at the upper end position.

Figure 32:
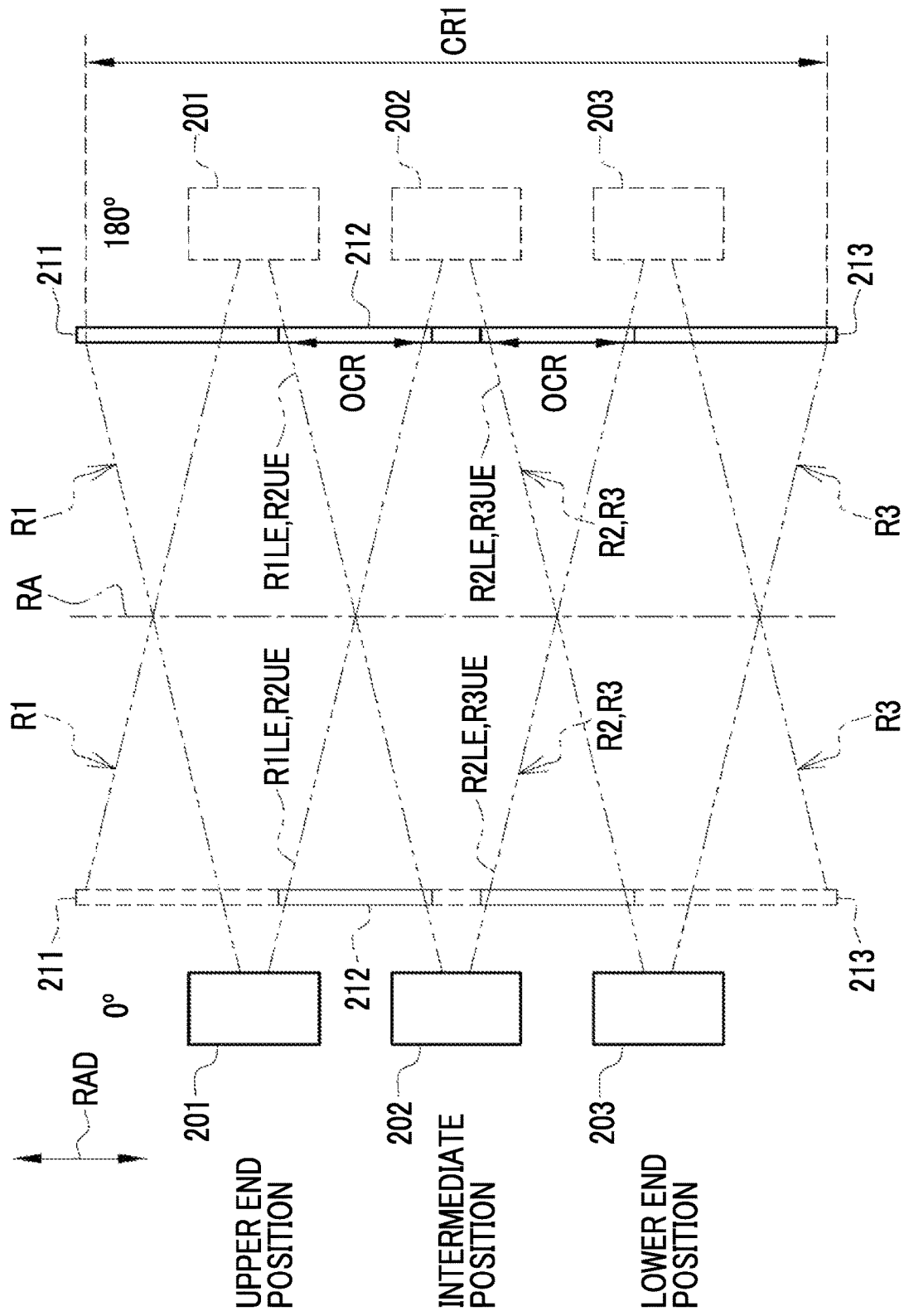
FIG. 32 is a diagram illustrating a flux of radiation in a case in which the first imaging unit is located at the upper end position, the second imaging unit is located at an intermediate position, and the third imaging unit is located at the lower end position.

For example, as illustrated in FIG. 32, the second radiation source 202 and the second radiation detector 212 constituting the second imaging unit 302 are disposed at intermediate positions, and the third radiation source 203 and the third radiation detector 213 constituting the third imaging unit 303 are disposed at the lower end positions. The intermediate position is a position where the lower end RILE of the flux of the first radiation R1 and the upper end R2UE of the flux of the second radiation R2 are matched with each other. The lower end position is a position where a lower end R2LE of the flux of the second radiation R2 and an upper end R3UE of a flux of third radiation R3 emitted from the third radiation source 203 are matched with each other. In this case, the first imaging range CR1 is a range having a width that is about twice the width W of the detection surface 58 of one radiation detector 21 in the rotation axis direction RAD. That is, the first imaging range CR1 is a range that exceeds the width W.

Figure 33:
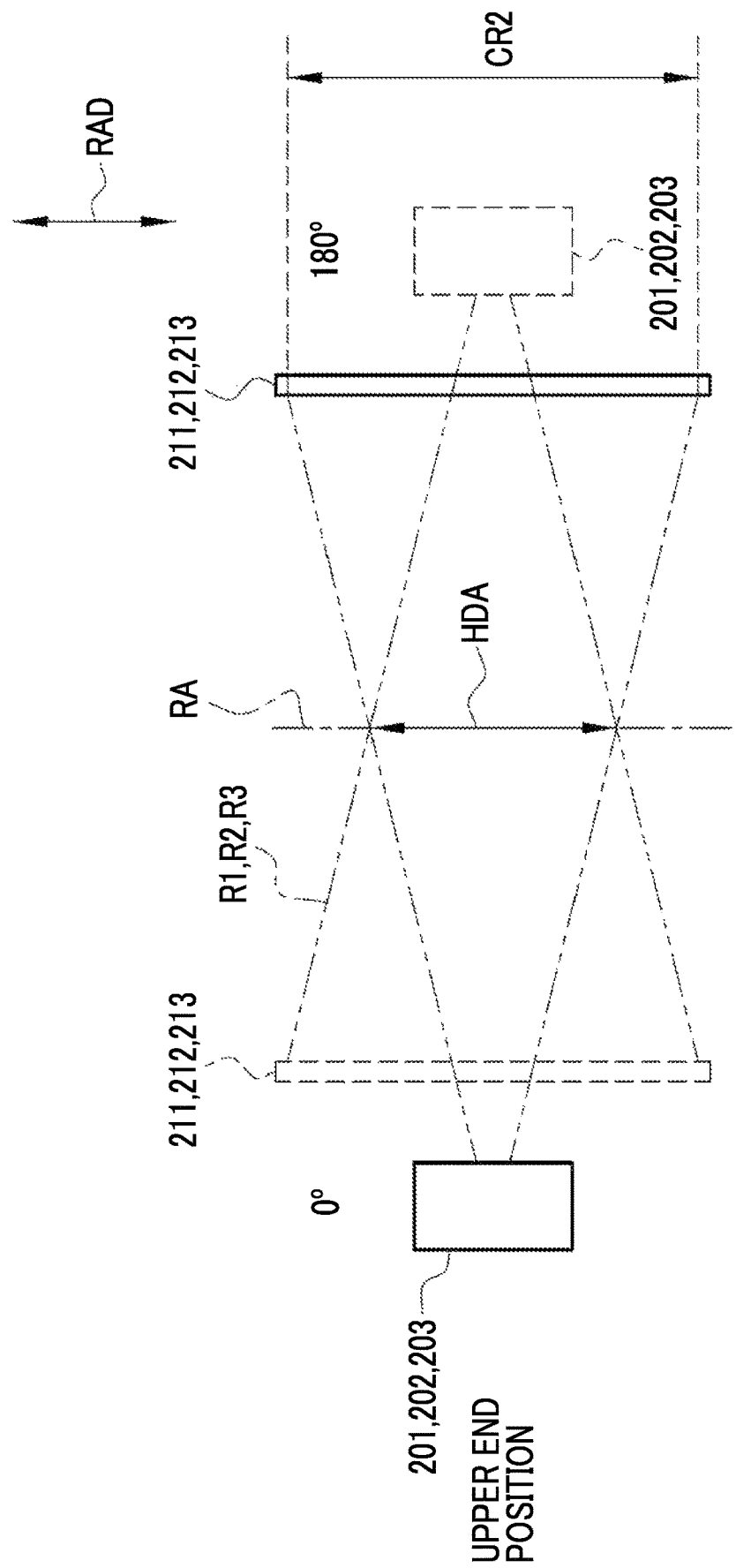
FIG. 33 is a diagram illustrating a flux of radiation in a case in which all of the first imaging unit, the second imaging unit, and the third imaging unit are located at the upper end positions.

For example, as illustrated in FIG. 33, in a case in which the second radiation source 202 and the second radiation detector 212, and the third radiation source 203 and the third radiation detector 213 are located at the upper end positions, the flux of the first radiation R1, the flux of the second radiation R2, and the radiation flux of the third radiation R3 are matched with one another. In this case, the second imaging range CR2 is a range that is matched with the width W of the detection surface 58 of one radiation detector 21 in the rotation axis direction RAD as in the case illustrated in FIG. 12 in the first embodiment. That is, the second imaging range CR2 is a range within the width W.

The content of the first imaging mode and the second imaging mode in the fifth embodiment is, for example, as illustrated in a table 155 in FIG. 34. That is, in the first imaging mode, imaging is performed in a state illustrated in FIG. 32 in which the height position of the second imaging unit 302 is the intermediate position, the height position of the third imaging unit 303 is the lower end position, and the imaging range is the first imaging range CR1 that exceeds the width W of the detection surface 58 of one radiation detector 21. The rotation angle, the rotation direction, the imaging time, and the frame rate are the same as those in the first imaging mode of the first embodiment.

In the second imaging mode, imaging is performed in a state illustrated in FIG. 33 in which the height positions of the second imaging unit 302 and the third imaging unit 303 are the upper end positions and the imaging range is the second imaging range CR2 within the width W of the detection surface 58 of one radiation detector 21. In this case, the rotation angle of the imaging unit 30 (frame 18) is 120°. Therefore, the imaging time is about 3.3 seconds. In addition, strictly speaking, the rotation angle is 120°+θ.

In the second imaging mode, 100 projection images are output from one radiation detector 21. In this example, since there are three imaging units 30 of the first imaging unit 301, the second imaging unit 302, and the third imaging unit 303, a total of 300 projection images can be obtained.

In the second imaging mode, the first imaging unit 301 is in charge of imaging in an angular range of 0° to 120°, the second imaging unit 302 is in charge of imaging in an angular range of 120° to 240°, and the third imaging unit 303 is in charge of imaging in an angular range of 240° to 360°. That is, the imaging of the entire circumference around the body axis of the subject S is shared by the first imaging unit 301, the second imaging unit 302, and the third imaging unit 303.

As described above, in the fifth embodiment, there are three imaging units 30 of the first imaging unit 301, the second imaging unit 302, and the third imaging unit 303. Therefore, it is possible to widen the first imaging range CR1 in the first imaging mode as compared to a case in which there are two imaging units 30. In addition, it is possible to perform imaging in the second imaging mode in a shorter time as compared to a case in which there are two imaging units 30.

Figure 35:
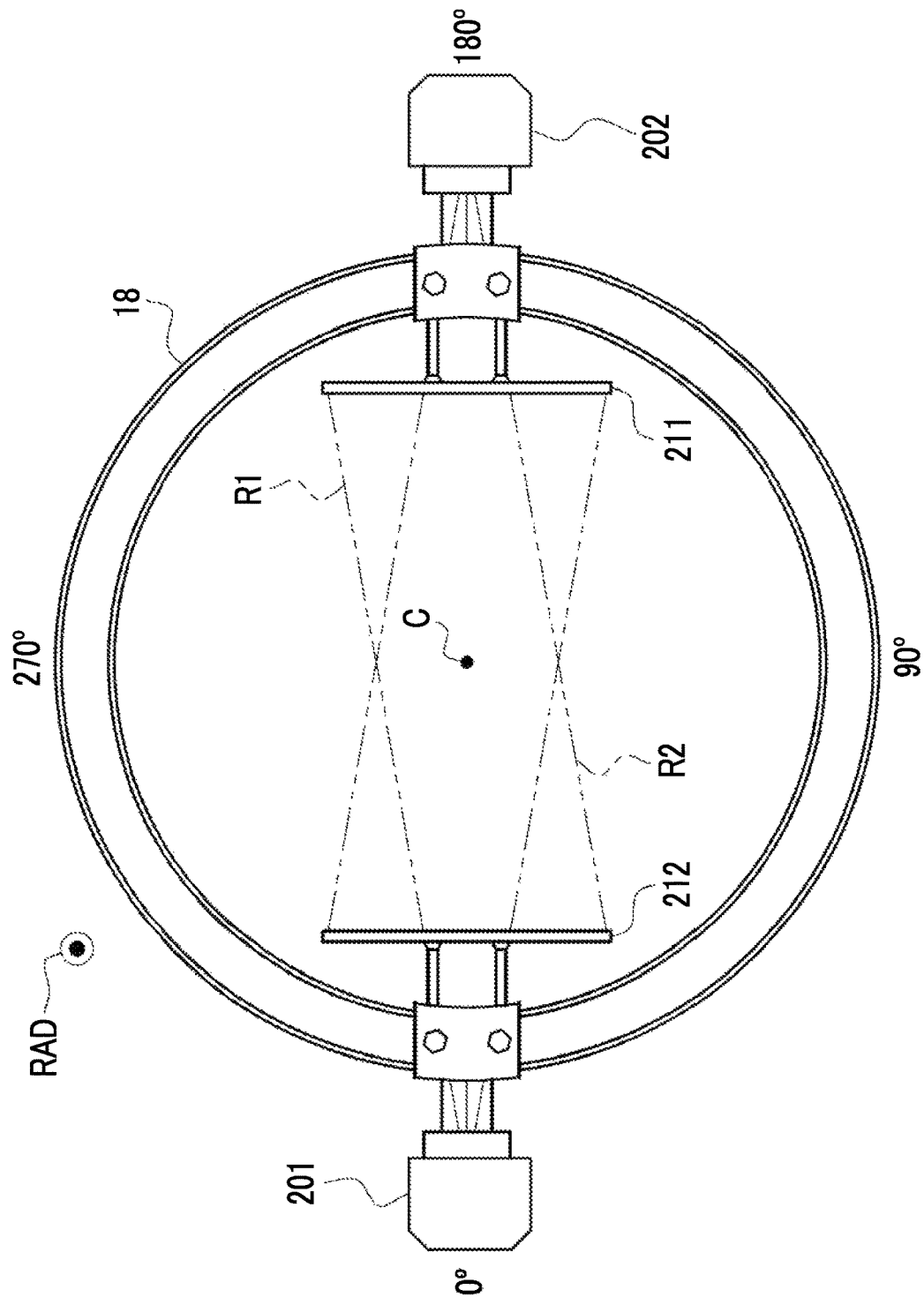
FIG. 35 is a diagram illustrating an example in which the first imaging unit and the second imaging unit are disposed at positions facing each other.

For example, as illustrated in FIG. 35, the first radiation source 201 and the second radiation source 202, and the first radiation detector 211 and the second radiation detector 212 may be disposed at positions (here, a position of 0° and a position of 180°) that face each other, as viewed from the rotation axis direction RAD. However, in this case, since the first radiation detector 211 and the second radiation detector 212 are included in the projection images, the positions where the first radiation source 201 and the second radiation source 202 are disposed in the rotation axis direction RAD are devised as follows.

Figure 36:
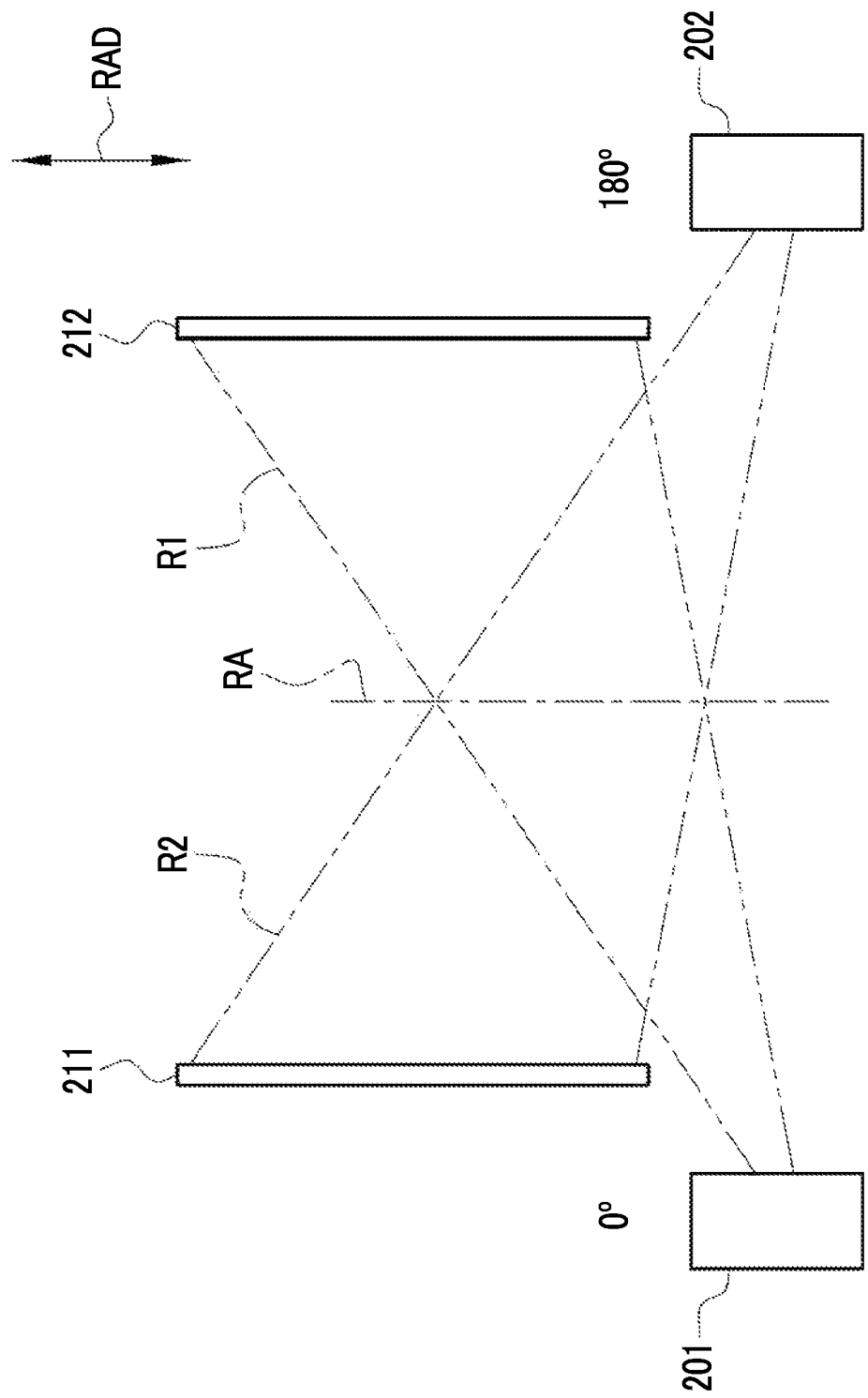
FIG. 36 is a diagram illustrating a flux of radiation in the second imaging mode in the case of the example illustrated in FIG. 35.

That is, for example, as illustrated in FIG. 36, in the case of the second imaging mode, the first radiation source 201 and the second radiation source 202 are disposed at positions that deviate downward from the first radiation detector 211 and the second radiation detector 212 in the rotation axis direction RAD. Then, the irradiation fields of the first radiation R1 and the second radiation R2 are adjusted by the irradiation field limiter 56 such that the first radiation R1 and the second radiation R2 are emitted to the first radiation detector 211 and the second radiation detector 212.

Figure 37:
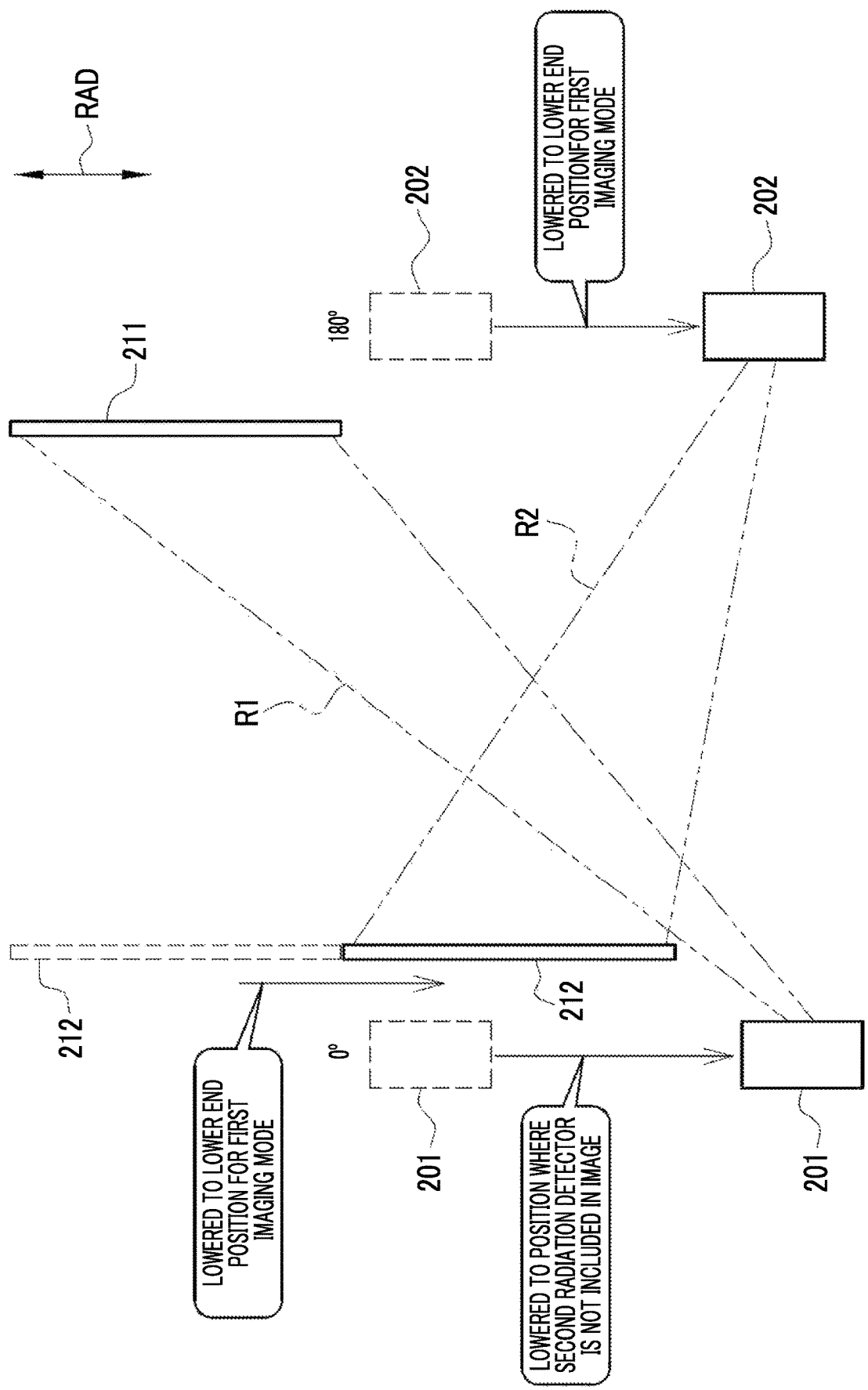
FIG. 37 is a diagram illustrating a flux of radiation in the first imaging mode in the case of the example illustrated in FIG. 35.

Further, for example, a case is considered in which the second radiation source 202 and the second radiation detector 212 are lowered to the lower end positions for the first imaging mode as illustrated in FIG. 37. In this configuration, in a case in which the first radiation source 201 remains at the position illustrated in FIG. 36, the lowered second radiation detector 212 is included in the projection image. Therefore, the radiation source elevating mechanism is also provided in the first radiation source 201 to lower the first radiation source 201 to the position where the second radiation detector 212 is not included in the projection image.

In this case, the second set angle, which is the rotation angle of the imaging unit 30 in the second imaging mode, may be 180°. Therefore, it is possible to complete imaging in the second imaging mode in a short time as compared to a case in which the second set angle of the first embodiment is 240°.

In addition, the frame 18 has a certain weight. Further, since the weight of the frame 18 is further increased by providing a plurality of imaging units 30, the inertial moment of the frame 18 is further increased. Therefore, for example, as illustrated in a graph of FIG. 38, in practice, an acceleration period AP from the start of rotation to constant-speed rotation and a deceleration period DP from the constant-speed rotation to the stop of the rotation are a time of T1-T0 and a time of T3-T2, respectively. Therefore, for example, in a case in which the frame 18 is rotated at the first set angle of 360° in the first imaging mode of the first embodiment, the frame 18 is rotated by 360° in a constant-speed period CSP, and each of the acceleration period AP and the deceleration period DP is ended with a rotation of 20°. Therefore, in practice, the frame 18 is rotated by 400°. In a case in which the frame 18 is rotated at, for example, the second set angle of 240° in the second imaging mode, similarly, the corresponding acceleration period AP and the corresponding deceleration period DP are provided, and the frame 18 is rotated by 240° or more.

Figure 38:
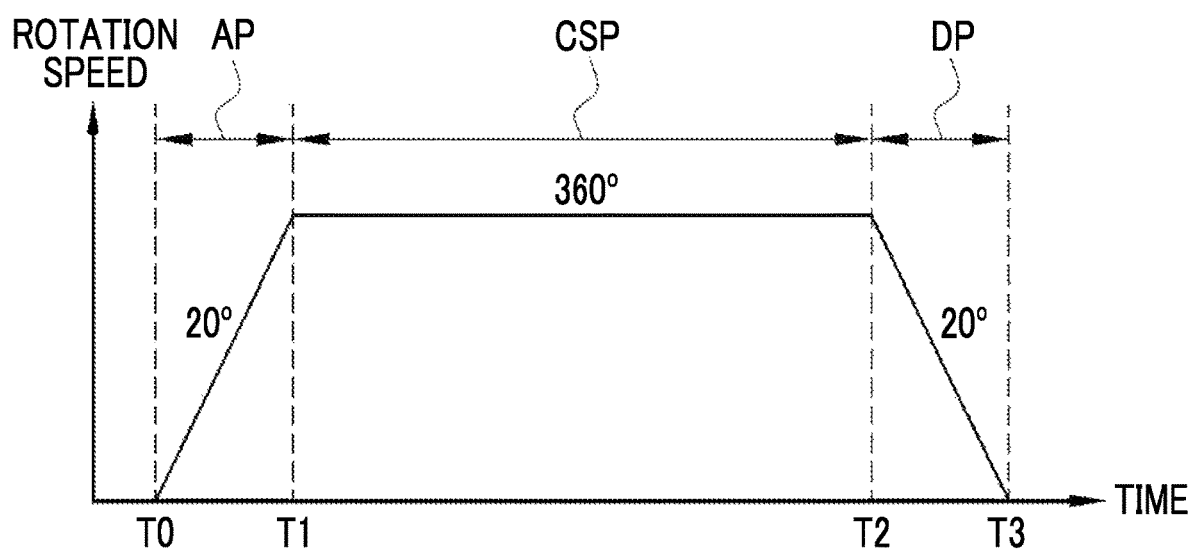
FIG. 38 is a graph illustrating a change in a rotation speed of a frame over time.

As described above, the frame 18 does not have a mechanism, such as a slip ring, and is supplied with power through a wiring line. Therefore, the frame 8 has a limit rotation angle corresponding to the length of the wiring line. Therefore, as a safety measure, it is preferable to provide a mechanical switch that forcibly cuts off the supply of power to the rotary motor 47 in a case in which the rotation angle of the frame 18 in one direction reaches the limit rotation angle. In a case in which the frame 18 is actually rotated by 400° for the 360° rotation of the frame 18 as illustrated in FIG. 38, a rotation angle converter for converting the rotation of 400° into the rotation of 360° may be connected to the potentiometer 48 of the rotation mechanism 45.

In the imaging in the first imaging mode, for example, in a case in which a wider range, such as the whole body, is imaged, the frame 18 may be raised and lowered two or more times to image the range in two or more steps. In addition, in a case in which a plurality of suspected parts at different height positions are specified in the imaging in the second imaging mode, similarly, the frame 18 may be raised and lowered two or more times to image the plurality of suspected parts one by one.

The imaging in the first imaging mode and the imaging in the second imaging mode may not be necessarily performed continuously. In a case in which a suspected part has already been specified by analyzing an image obtained by another medical imaging apparatus, such as a simple radiography apparatus or an ultrasonography apparatus, only the imaging in the second imaging mode may be performed.

In the first embodiment, the first imaging unit 301 is fixed at the upper end position. However, the present disclosure is not limited thereto. The radiation source elevating mechanism and the detector elevating mechanism may also be provided in the first imaging unit 301 to raise and lower the first imaging unit 301 in the rotation axis direction RAD.

A mechanism that moves the radiation source 20 and the radiation detector 21 along a circumferential direction of the frame 18 may be provided to change the positions where the radiation source 20 and the radiation detector 21 are disposed. This configuration makes it possible to retract the radiation source 20 and the radiation detector 21 that interfere with the guidance of the subject S into the apparatus main body 11 to positions that do not interfere with the guidance.

Instead of specifying the suspected part with the image analysis unit 114, the tomographic image obtained by the imaging in the first imaging mode may be displayed on the display 98 such that the operator designates the suspected part on the screen.

The number of columns 14 may be four or five. Further, a stepping motor may be used as the rotary motor 47, and the rotation position of the frame 18 may be determined by the number of pulses applied to the rotary motor 47. Furthermore, the frame 18 is not limited to the circular ring and may be a polygonal ring.

The hardware configuration of the computer constituting the control device 12 can be modified in various ways. For example, the control device 12 may be configured by a plurality of computers separated as hardware in order to improve processing capacity and reliability. For example, the functions of the receiving unit 110, the RW control unit 111, and the display control unit 115 and the functions of the imaging control unit 112, the image processing unit 113, and the image analysis unit 114 are distributed to two computers. In this case, the two computers constitute the control device 12.

As described above, the hardware configuration of the computer of the control device 12 can be appropriately changed according to required performances, such as processing capacity, safety, and reliability. Further, not only the hardware but also an application program, such as the operation program 105, may be duplicated or may be dispersively stored in a plurality of storages in order to secure safety and reliability.

In each of the above-described embodiments, for example, the following various processors can be used as the hardware structure of processing units performing various processes, such as the receiving unit 110, the RW control unit 111, the imaging control unit 112, the image processing unit 113, the image analysis unit 114, and the display control unit 115. The various processors include, for example, the CPU 97 which is a general-purpose processor executing software (operation program 105) to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or by a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As described above, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the techniques described in the following supplementary notes from the above description.

Supplementary Note 1

A computed tomography apparatus comprising:
a plurality of imaging units each of which includes a radiation source that emits radiation having a quadrangular pyramid shape to a subject and a radiation detector in which a plurality of pixels detecting the radiation transmitted through the subject are two-dimensionally arranged;
a rotation mechanism that rotates the plurality of imaging units around a body axis of the subject;
a displacement mechanism that changes an interval between the plurality of imaging units in a rotation axis direction; and
a processor that controls operations of the plurality of imaging units, the rotation mechanism, and the displacement mechanism.

Supplementary Note 2

The computed tomography apparatus according to Supplementary Note 1,
wherein the processor controls switching between a first imaging mode in which the interval is relatively large for imaging and a second imaging mode in which the interval is relatively small for imaging.

Supplementary Note 3

The computed tomography apparatus according to Supplementary Note 2,
wherein the first imaging mode is a mode in which a first imaging range that exceeds a width of a detection surface for the radiation in the radiation detector is imaged, and
a rotation angle of the plurality of imaging units around the body axis in the first imaging mode is a first set angle that is equal to or greater than 180°.

Supplementary Note 4

The computed tomography apparatus according to Supplementary Note 3,
wherein the processor sets the interval such that an overlapping imaging range occurs between projection images obtained by the imaging units adjacent to each other, performs a reconstruction process on the projection images obtained from each of the plurality of imaging units to generate a plurality of tomographic images for each of the plurality of imaging units, and registers the plurality of tomographic images on the basis of the overlapping imaging range to combine the plurality of tomographic images.

Supplementary Note 5

The computed tomography apparatus according to any one of Supplementary Notes 2 to 4,
wherein the plurality of imaging units have different phases in a rotation direction,
the second imaging mode is a mode in which a second imaging range within the width of the detection surface for the radiation in the radiation detector is imaged,
a rotation angle of the plurality of imaging units around the body axis in the second imaging mode is a second set angle corresponding to the phases of the plurality of imaging units in the rotation direction, and
the plurality of imaging units are rotated at the second set angle such that imaging of an entire circumference around the body axis is shared by the plurality of imaging units.

Supplementary Note 6

The computed tomography apparatus according to any one of Supplementary Notes 2 to 5,
wherein, in a case in which the first imaging mode and the second imaging mode are continuously performed, the processor rotates the plurality of imaging units in a first direction in the first imaging mode and rotates the plurality of imaging units in a second direction opposite to the first direction in the second imaging mode.

Supplementary Note 7

The computed tomography apparatus according to any one of Supplementary Notes 2 to 6,
wherein the first imaging mode includes a plurality of sub-imaging modes in which the intervals are different.

Supplementary Note 8

The computed tomography apparatus according to any one of Supplementary Notes 1 to 7,
wherein the radiation detector is disposed at an offset position that is separated from a reference position facing the radiation source by a preset angle as viewed from the rotation axis direction.

Supplementary Note 9

The computed tomography apparatus according to any one of Supplementary Notes 1 to 8, wherein the plurality of imaging units are held in a frame, the subject is positioned in the frame, and
the radiation source is disposed outside the frame, and the radiation detector is disposed inside the frame as viewed from the rotation axis direction.

Supplementary Note 10

The computed tomography apparatus according to any one of Supplementary Notes 1 to 9,
wherein the plurality of imaging units are two imaging units of a first imaging unit and a second imaging unit, and
in a case in which a position where a first radiation source of the first imaging unit is disposed is 0° as viewed from the rotation axis direction, a second radiation source of the second imaging unit is disposed at a position separated from the first radiation source by an angle that is equal to or greater than 90° and equal to or less than 120°.

Supplementary Note 11

The computed tomography apparatus according to any one of Supplementary Notes 1 to 10,
wherein the plurality of imaging units are three imaging units.

Supplementary Note 12

The computed tomography apparatus according to any one of Supplementary Notes 1 to 11,
wherein the displacement mechanism has an electric mode in which the imaging unit is moved by an electric actuator and a manual mode in which the imaging unit is manually moved.

Supplementary Note 13

The computed tomography apparatus according to Supplementary Note 12,
wherein, in the manual mode, the processor performs control to issue a warning in a case in which the interval is equal to or greater than a threshold value.

Supplementary Note 14

The computed tomography apparatus according to any one of Supplementary Notes 1 to 13, further comprising:
a camera that is moved in operative association with the imaging unit,
wherein the processor performs control to display a camera image obtained from the camera on a display.

Supplementary Note 15

The computed tomography apparatus according to Supplementary Note 14,
wherein the processor displays an imaging range that is reconstructible as a tomographic image to be superimposed on the camera image.

Supplementary Note 16

The computed tomography apparatus according to any one of Supplementary Notes 1 to 15,
wherein the subject is positioned in either a standing posture or a sitting posture.

In the technology of the present disclosure, the above-described various embodiments and/or various modification examples may be combined with each other as appropriate. In addition, the present disclosure is not limited to the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions related to the technology of the present disclosure. Therefore, unnecessary portions may be deleted or new elements may be added or replaced in the above descriptions and illustrations without departing from the gist of the technology of the present disclosure. In addition, in the above descriptions and illustrations, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. A computed tomography apparatus comprising:
a plurality of imaging units each of which includes a radiation source that emits radiation having a quadrangular pyramid shape to a subject and a radiation detector in which a plurality of pixels detecting the radiation transmitted through the subject are two-dimensionally arranged;
a rotation mechanism that rotates the plurality of imaging units around a body axis of the subject;
a displacement mechanism that changes an interval between the plurality of imaging units in a rotation axis direction; and
a processor that controls operations of the plurality of imaging units, the rotation mechanism, and the displacement mechanism.

2. The computed tomography apparatus according to claim 1,
wherein the processor controls switching between a first imaging mode in which the interval is relatively large for imaging and a second imaging mode in which the interval is relatively small for imaging.

3. The computed tomography apparatus according to claim 2, wherein the first imaging mode is a mode in which a first imaging range that exceeds a width of a detection surface for the radiation in the radiation detector is imaged, and a rotation angle of the plurality of imaging units around the body axis in the first imaging mode is a first set angle that is equal to or greater than 180°.

4. The computed tomography apparatus according to claim 3, wherein the processor sets the interval such that an overlapping imaging range occurs between projection images obtained by the imaging units adjacent to each other, performs a reconstruction process on the projection images obtained from each of the plurality of imaging units to generate a plurality of tomographic images for each of the plurality of imaging units, and registers the plurality of tomographic images on the basis of the overlapping imaging range to combine the plurality of tomographic images.

5. The computed tomography apparatus according to claim 2, wherein the plurality of imaging units have different phases in a rotation direction, the second imaging mode is a mode in which a second imaging range within the width of the detection surface for the radiation in the radiation detector is imaged, a rotation angle of the plurality of imaging units around the body axis in the second imaging mode is a second set angle corresponding to the phases of the plurality of imaging units in the rotation direction, and the plurality of imaging units are rotated at the second set angle such that imaging of an entire circumference around the body axis is shared by the plurality of imaging units.

6. The computed tomography apparatus according to claim 2, wherein, in a case in which the first imaging mode and the second imaging mode are continuously performed, the processor rotates the plurality of imaging units in a first direction in the first imaging mode and rotates the plurality of imaging units in a second direction opposite to the first direction in the second imaging mode.

7. The computed tomography apparatus according to claim 2, wherein the first imaging mode includes a plurality of sub-imaging modes in which the intervals are different.

8. The computed tomography apparatus according to claim 1, wherein the radiation detector is disposed at an offset position that is separated from a reference position facing the radiation source by a preset angle as viewed from the rotation axis direction.

9. The computed tomography apparatus according to claim 1, wherein the plurality of imaging units are held in a frame, the subject is positioned in the frame, and the radiation source is disposed outside the frame, and the radiation detector is disposed inside the frame as viewed from the rotation axis direction.

10. The computed tomography apparatus according to claim 1, wherein the plurality of imaging units are two imaging units of a first imaging unit and a second imaging unit, and in a case in which a position where a first radiation source of the first imaging unit is disposed is 0° as viewed from the rotation axis direction, a second radiation source of the second imaging unit is disposed at a position separated from the first radiation source by an angle that is equal to or greater than 90° and equal to or less than 120°.

11. The computed tomography apparatus according to claim 1, wherein the plurality of imaging units are three imaging units.

12. The computed tomography apparatus according to claim 1, wherein the displacement mechanism has an electric mode in which the imaging unit is moved by an electric actuator and a manual mode in which the imaging unit is manually moved.

13. The computed tomography apparatus according to claim 12, wherein, in the manual mode, the processor performs control to issue a warning in a case in which the interval is equal to or greater than a threshold value.

14. The computed tomography apparatus according to claim 1, further comprising:

a camera that is moved in operative association with the imaging unit, wherein the processor performs control to display a camera image obtained from the camera on a display.

15. The computed tomography apparatus according to claim 14, wherein the processor displays an imaging range that is reconstructible as a tomographic image to be superimposed on the camera image.

16. The computed tomography apparatus according to claim 1, wherein the subject is positioned in either a standing posture or a sitting posture.

* * * * *